(12) United States Patent
Beckman et al.

(10) Patent No.: US 7,670,299 B2
(45) Date of Patent: Mar. 2, 2010

(54) DEVICE FOR MINIMALLY INVASIVE INTERNAL TISSUE REMOVAL

(75) Inventors: Andrew T. Beckman, Cincinnati, OH (US); Gwendolyn Perez Payne, Cincinnati, OH (US); Lee Reichel, Springboro, OH (US)

(73) Assignee: Ethincon Endo-Surgery, Inc., Cincinnati, OH (US)

( * ) Notice: Subject to any disclaimer, the term of this patent is extended or adjusted under 35 U.S.C. 154(b) by 215 days.

(21) Appl. No.: 11/369,587

(22) Filed: Mar. 7, 2006

(65) Prior Publication Data

US 2007/0213755 A1    Sep. 13, 2007

(51) Int. Cl.
*A61B 10/00* (2006.01)
*A61B 17/32* (2006.01)

(52) U.S. Cl. .................. 600/566; 600/567; 606/170

(58) Field of Classification Search ......... 600/562–568; 606/170–171
See application file for complete search history.

(56) References Cited

U.S. PATENT DOCUMENTS

| | | | |
|---|---|---|---|
| 1,867,624 A | | 7/1932 | Hoffman |
| 2,716,035 A | | 8/1955 | Thorndike |
| 3,003,235 A | | 10/1961 | Temple et al. |
| 3,328,876 A | | 7/1967 | Hoppe |
| 3,330,268 A | | 7/1967 | Goldsmith |
| 3,364,572 A | | 1/1968 | Hoppe |
| 3,372,477 A | | 3/1968 | Hoppe |
| 3,470,867 A | * | 10/1969 | Goldsmith .............. 600/566 |
| 3,561,429 A | | 2/1971 | Jewett et al. |
| 3,606,878 A | | 9/1971 | Kellogg, Jr. |
| 3,800,783 A | | 4/1974 | Jamshidi |
| 3,802,074 A | | 4/1974 | Hoppe |
| 3,815,604 A | | 6/1974 | O'Malley et al. |
| 3,877,434 A | | 4/1975 | Ferguson et al. |
| 3,929,123 A | | 12/1975 | Jamshidi |
| 3,995,619 A | | 12/1976 | Glatzer |
| 4,011,869 A | | 3/1977 | Seiler, Jr. |

(Continued)

FOREIGN PATENT DOCUMENTS

DE    10050742    4/2001

(Continued)

OTHER PUBLICATIONS

European Search Report for Application No. 07250933 dated Sep. 7, 2007.

(Continued)

*Primary Examiner*—Max Hindenburg
*Assistant Examiner*—John Pani

(57) ABSTRACT

A medical device for severing and removing small amounts of internal tissue for biopsy sampling or other purposes is disclosed. Versions of the device may include a hollow probe having a piecing tip, a tissue receiving aperture and a vacuum lumen; a cutter within the probe having a cutting edge that moves past the tissue receiving aperture, and a cutter driver mechanism. A cutter for use with versions disclosed herein may include an angled cutting tip and a cutting edge having a concave grind. Versions of the device also may include an aspirator fluidly connected to the vacuum lumen, coordinated operation of the aspirator and the cutter driver mechanism, and a fluid management system. Versions described may be used for removing multiple samples of tissue during a single insertion of the probe proximate to a target tissue mass.

15 Claims, 19 Drawing Sheets

U.S. PATENT DOCUMENTS

| | | | |
|---|---|---|---|
| 4,051,852 A | 10/1977 | Villari | |
| 4,099,529 A | 7/1978 | Peyman | |
| 4,111,207 A | 9/1978 | Seiler, Jr. | |
| 4,210,146 A | 7/1980 | Banko | |
| 4,530,356 A * | 7/1985 | Helfgott et al. | 606/171 |
| 4,577,629 A | 3/1986 | Martinez | |
| 4,598,710 A | 7/1986 | Kleinberg et al. | |
| 4,753,234 A | 6/1988 | Martinez | |
| 4,819,635 A | 4/1989 | Shapiro | |
| 4,844,088 A * | 7/1989 | Kambin | 600/566 |
| 4,900,300 A | 2/1990 | Lee | |
| 4,961,430 A | 10/1990 | Sheahon | |
| 5,015,250 A | 5/1991 | Foster | |
| 5,084,058 A | 1/1992 | Li | |
| 5,087,263 A | 2/1992 | Li | |
| 5,106,364 A | 4/1992 | Hayafuji et al. | |
| 5,133,723 A | 7/1992 | Li et al. | |
| 5,163,946 A | 11/1992 | Li | |
| 5,213,110 A * | 5/1993 | Kedem et al. | 600/567 |
| 5,312,422 A | 5/1994 | Trott | |
| 5,320,110 A * | 6/1994 | Wang | 600/566 |
| 5,324,298 A | 6/1994 | Phillips et al. | |
| 5,335,671 A | 8/1994 | Clement | |
| 5,405,354 A | 4/1995 | Sarrett | |
| 5,439,467 A | 8/1995 | Benderev et al. | |
| 5,469,860 A | 11/1995 | DeSantis | |
| 5,474,565 A | 12/1995 | Trott | |
| 5,511,556 A | 4/1996 | DeSantis | |
| 5,526,822 A | 6/1996 | Burbank et al. | |
| 5,536,273 A | 7/1996 | Lehrer | |
| 5,560,373 A | 10/1996 | DeSantis et al. | |
| 5,591,177 A | 1/1997 | Lehrer | |
| 5,609,597 A | 3/1997 | Lehrer | |
| 5,649,547 A | 7/1997 | Ritchart et al. | |
| 5,674,232 A * | 10/1997 | Halliburton | 606/159 |
| 5,720,760 A | 2/1998 | Becker et al. | |
| 5,769,086 A | 6/1998 | Ritchart et al. | |
| 5,775,333 A * | 7/1998 | Burbank et al. | 600/567 |
| 5,817,033 A | 10/1998 | DeSantis et al. | |
| 5,928,164 A | 7/1999 | Burbank et al. | |
| 5,944,673 A | 8/1999 | Gregoire et al. | |
| 5,964,716 A | 10/1999 | Gregoire et al. | |
| 5,971,939 A | 10/1999 | DeSantis et al. | |
| 5,980,469 A | 11/1999 | Burbank et al. | |
| 6,007,497 A | 12/1999 | Huitema | |
| 6,017,316 A | 1/2000 | Ritchart et al. | |
| 6,027,514 A | 2/2000 | Stine et al. | |
| 6,077,230 A * | 6/2000 | Gregoire et al. | 600/566 |
| 6,086,544 A | 7/2000 | Hibner et al. | |
| 6,120,462 A | 9/2000 | Hibner et al. | |
| 6,143,006 A | 11/2000 | Chan | |
| 6,228,055 B1 | 5/2001 | Foerster et al. | |
| 6,231,522 B1 | 5/2001 | Voegele et al. | |
| 6,273,862 B1 | 8/2001 | Privitera et al. | |
| 6,280,447 B1 | 8/2001 | Marino et al. | |
| 6,361,504 B1 * | 3/2002 | Shin | 600/562 |
| 6,471,659 B2 | 10/2002 | Eggers et al. | |
| 6,471,700 B1 | 10/2002 | Burbank et al. | |
| 6,494,844 B1 | 12/2002 | Van Bladel et al. | |
| 6,514,215 B1 | 2/2003 | Ouchi | |
| 6,517,498 B1 | 2/2003 | Burbank et al. | |
| 6,540,694 B1 | 4/2003 | Van Bladel et al. | |
| 6,540,695 B1 | 4/2003 | Burbank et al. | |
| 6,551,255 B2 | 4/2003 | Van Bladel et al. | |
| 6,554,779 B2 | 4/2003 | Viola et al. | |
| 6,557,196 B2 | 5/2003 | Falbo, Sr. et al. | |
| 6,585,664 B2 | 7/2003 | Burdorff et al. | |
| 6,592,610 B2 | 7/2003 | Beyar | |
| 6,602,203 B2 | 8/2003 | Stephens | |
| 6,610,020 B2 | 8/2003 | Voegele | |
| 6,620,111 B2 | 9/2003 | Stephens et al. | |
| 6,626,849 B2 | 9/2003 | Huitema et al. | |
| 6,626,903 B2 | 9/2003 | McGuckin et al. | |
| 6,629,986 B1 | 10/2003 | Ross et al. | |
| 6,656,133 B2 | 12/2003 | Voegele et al. | |
| 6,689,072 B2 | 2/2004 | Kaplan et al. | |
| 6,695,852 B2 | 2/2004 | Gleason | |
| 6,699,206 B2 | 3/2004 | Burbank et al. | |
| 6,709,408 B2 | 3/2004 | Fisher | |
| 6,712,773 B1 | 3/2004 | Viola | |
| 6,712,775 B2 | 3/2004 | Burbank et al. | |
| 6,714,808 B2 | 3/2004 | Klimberg et al. | |
| 6,716,224 B2 | 4/2004 | Singhatat | |
| 6,730,044 B2 | 5/2004 | Stephens et al. | |
| 6,730,045 B2 | 5/2004 | Finer | |
| 6,733,509 B2 | 5/2004 | Nobles et al. | |
| 6,752,768 B2 | 6/2004 | Burdorff et al. | |
| 6,852,108 B2 | 2/2005 | Barry et al. | |
| 6,860,860 B2 | 3/2005 | Viola | |
| 6,872,185 B2 | 3/2005 | Fisher | |
| 6,890,309 B2 | 5/2005 | Fisher | |
| 6,908,440 B2 | 6/2005 | Fisher | |
| 6,923,809 B2 | 8/2005 | Eggers et al. | |
| 6,942,627 B2 | 9/2005 | Huitema | |
| 6,945,942 B2 | 9/2005 | Van Bladel et al. | |
| 7,419,472 B2 | 9/2008 | Hibner et al. | |
| 2001/0041901 A1 | 11/2001 | Furusawa | |
| 2001/0053916 A1 | 12/2001 | Rioux | |
| 2002/0049458 A1 | 4/2002 | Singhatat | |
| 2002/0050277 A1 | 5/2002 | Beyar | |
| 2002/0087178 A1 | 7/2002 | Nobles et al. | |
| 2003/0139752 A1 | 7/2003 | Pasricha et al. | |
| 2003/0199753 A1 | 10/2003 | Hibner et al. | |
| 2004/0153003 A1 | 8/2004 | Cicenas et al. | |
| 2004/0167428 A1 * | 8/2004 | Quick et al. | 600/564 |
| 2005/0165328 A1 | 7/2005 | Heske | |

FOREIGN PATENT DOCUMENTS

| | | |
|---|---|---|
| EP | 0582005 | 2/1994 |
| EP | 0890339 | 1/1999 |
| EP | 0970658 | 1/2000 |
| EP | 1520518 | 4/2005 |
| GB | 815046 | 6/1959 |
| SU | 1225547 | 4/1986 |
| SU | 001834651 | 8/1993 |
| WO | WO 96/24289 | 8/1996 |

OTHER PUBLICATIONS

European Search Report dated Nov. 14, 2007 for EP Application 07250926.

European Search Report and Communication dated Aug. 27, 2007 for Application No. 07250926.8.

Non-Final Rejection dated Sep. 5, 2008 for U.S. Appl. No. 11/369,588.

* cited by examiner

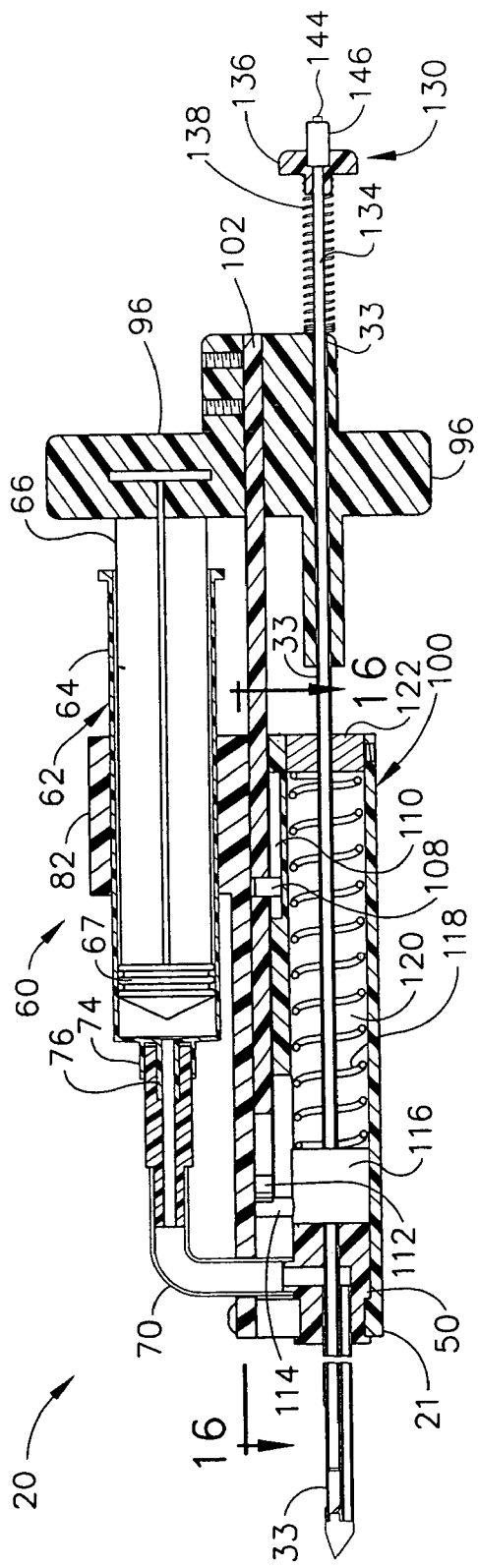
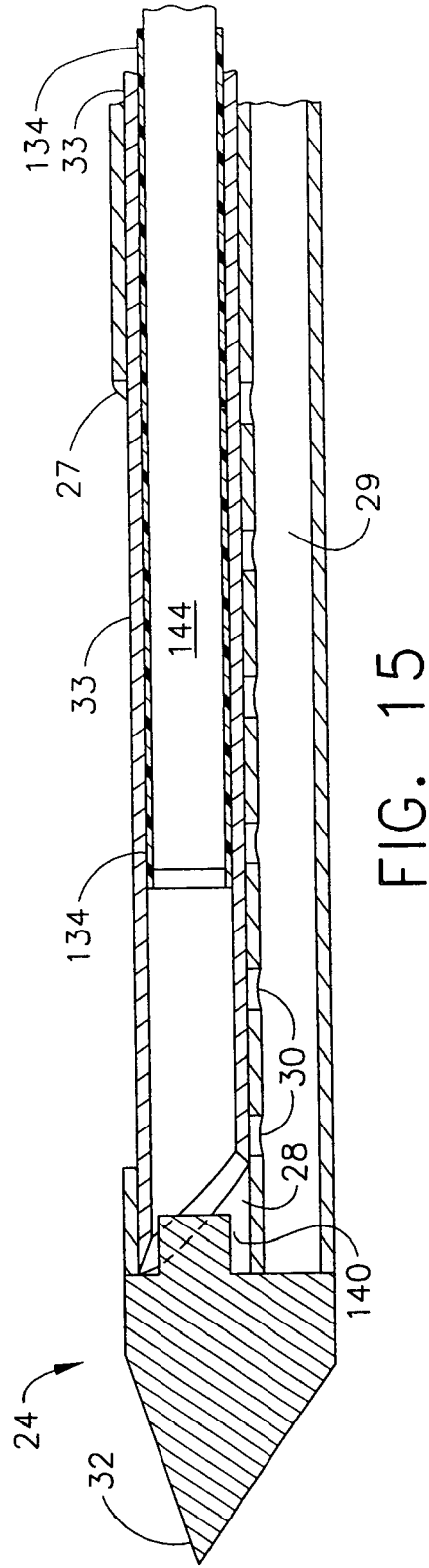
FIG. 14
FIG. 15

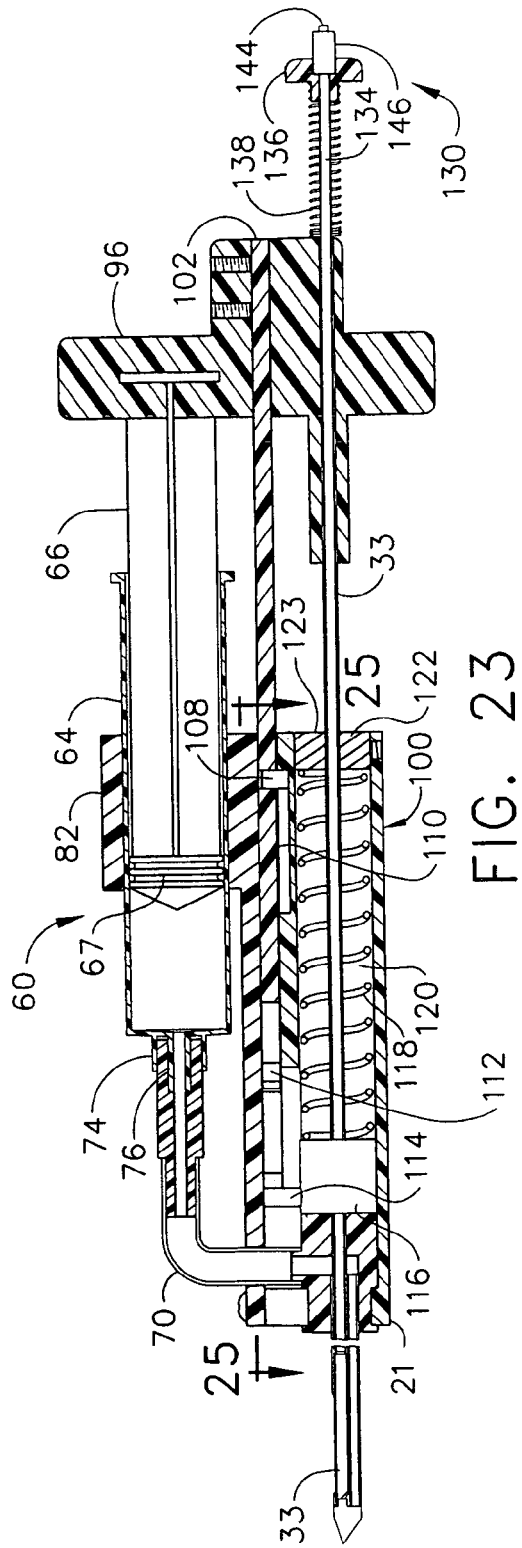
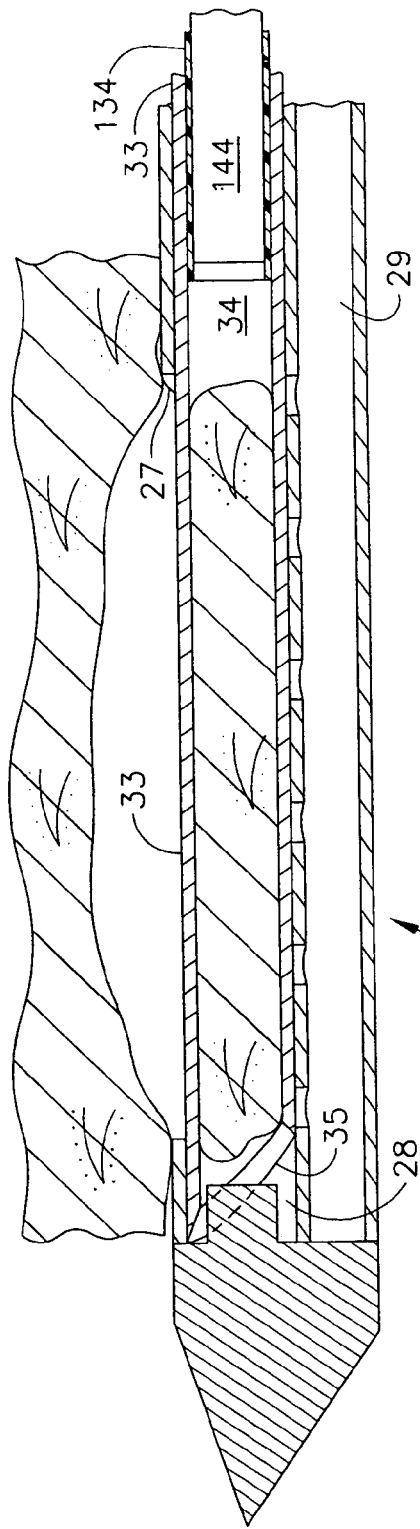
FIG. 23
FIG. 24

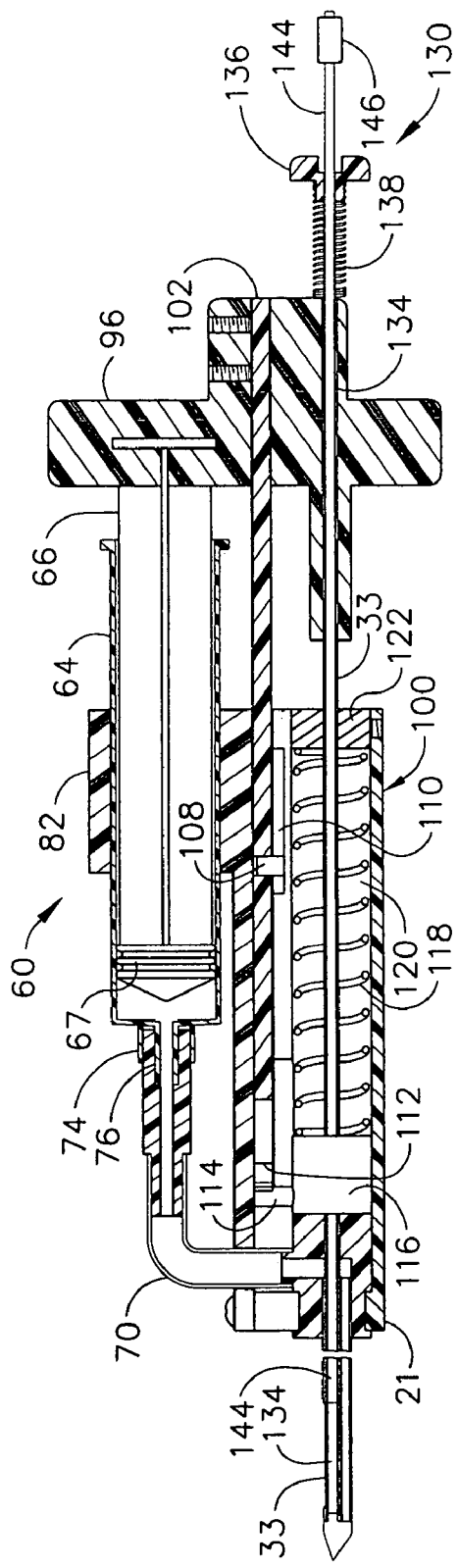
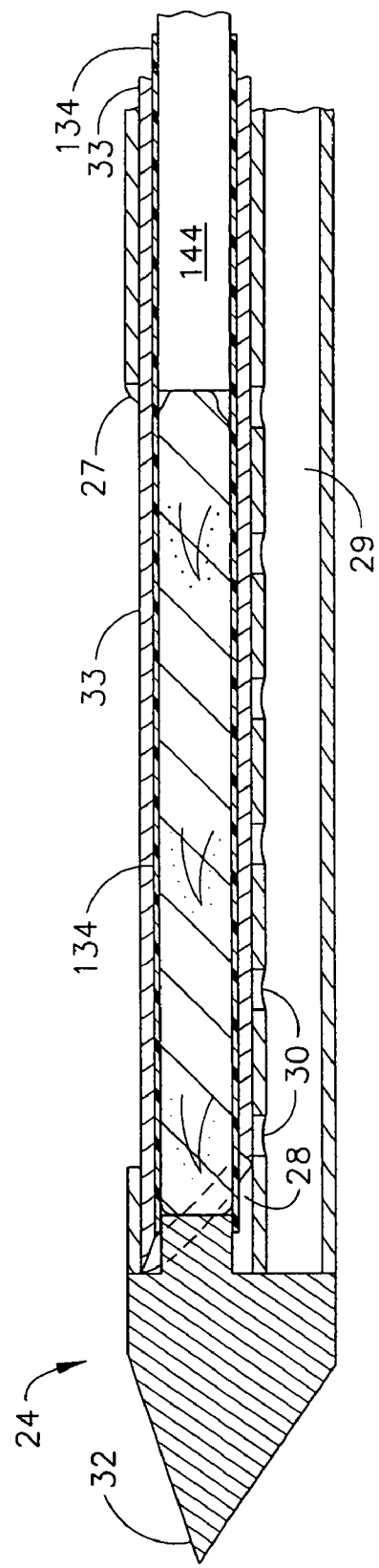
FIG. 26
FIG. 27

DEVICE FOR MINIMALLY INVASIVE INTERNAL TISSUE REMOVAL

BACKGROUND

Devices utilizing hollow probe aspiration are useful for removing and/or obtaining samples of tissue in minimally invasive percutaneous procedures, for biopsy or other purposes, such as therapeutic tissue removal purposes.

It may be desirable to provide additional and alternative designs for an instrument including a hollow probe that allows for effective and efficient sample cutting and removal, minimal trauma to tissue and to the patient in the tissue removal procedure, and of relatively simple design, manufacture and use.

A variety of such devices have been developed and used, but to the best of the inventors' knowledge, no one prior to the inventors has created or used the invention described in the appended claims.

BRIEF DESCRIPTION OF THE FIGURES

While the specification concludes with claims that particularly point out and distinctly claim the invention, it is believed the present invention will be better understood from the following description taken in conjunction with the accompanying drawings, in which like reference numerals identify the same elements. The drawings and detailed description which follow are intended to be merely illustrative and are not intended to limit the scope of the invention as set forth in the appended claims.

FIG. 14 presents a side longitudinal cross-sectional view of the device of FIG. 1, in a pre-deployment position;

FIG. 15 presents a side longitudinal cross-sectional view of the probe as shown in FIG. 14;

FIG. 23 presents a side longitudinal cross-sectional view of the device of FIG. 1, in a fired position;

FIG. 24 presents a side longitudinal cross-sectional view of the probe shown in FIG. 23, and after tissue has been severed and captured within the probe;

FIG. 26 presents a side longitudinal cross-sectional view of the device of FIG. 1, during collection of severed tissue;

FIG. 27 presents a side longitudinal cross-sectional view of the probe as shown in FIG. 26.

DETAILED DESCRIPTION OF EMBODIMENTS OF THE INVENTION

Versions of a device described and illustrated herein are directed to an efficient system and method for removing tissue in a minimally invasive procedure for biopsy sampling or other purposes. In particular, versions described herein are directed to a device having a hollow probe with a receiving aperture, and a cutter within the probe having a cutting tip, for efficiently drawing in, cutting and removing tissue in a percutaneous procedure. Providing a cutter with an angled and rounded cutting tip, such as described with respect to the exemplary versions herein, may allow for effective cutting of tissue with a predominantly axial motion of the cutter.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

For purposes of the description contained herein, with respect to components described herein, the term "integral" refers to two or more identifiable components that are either formed as a single unit or, alternatively, are otherwise joined or attached together such that they move and/or operate substantially as a single unit. The term "integral" is not intended to be limited to identifiable components that are continuous or formed from a homogeneous continuum of material. However, it should be understood that the identification of separately identifiable components joined together so as to operate substantially integrally is not meant to imply that separately identifiable components are necessarily required, and is not intended to limit the scope of the claims.

For purposes of the description contained herein, "vacuum" means pressure within a space that is lower by any amount than atmospheric or ambient pressure, and although not exclusive of a condition of absolute vacuum defined by a complete absence within a space of air, fluid or other matter, the term as used herein is not meant to require or be limited to such a condition.

Figure 1:
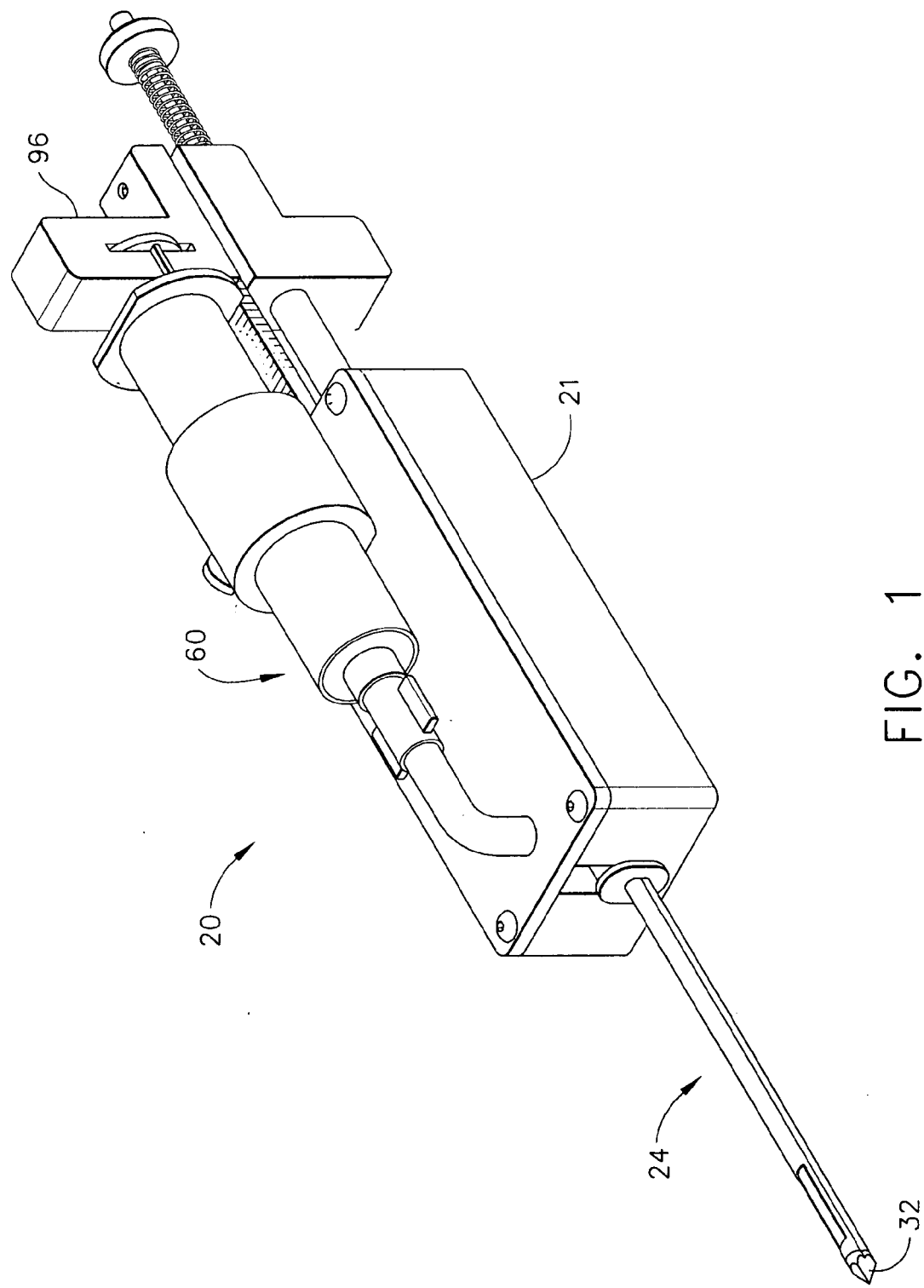
FIG. 1 presents a perspective view of one version of a device for severing internal tissues and removing the severed tissues.

Turning to the drawings, FIG. 1 illustrates one example of a device for severing internal tissues and removing the severed tissues. Device 20 includes a probe 24, having a distal end and a proximal end, where the proximal end is affixed by any suitable mechanism to a body 21. Body 21 may be shaped as shown, or alternatively may be shaped to be aesthetically attractive and/or to form a handle or other conveniently grasped shape, or may have other features, for example, for mounting within or to suitable insertion-guiding, holding and/or steadying or immobilizing devices or fixtures. Versions of the probe 24 and body 21 will be discussed in greater detail herein.

Figure 2:
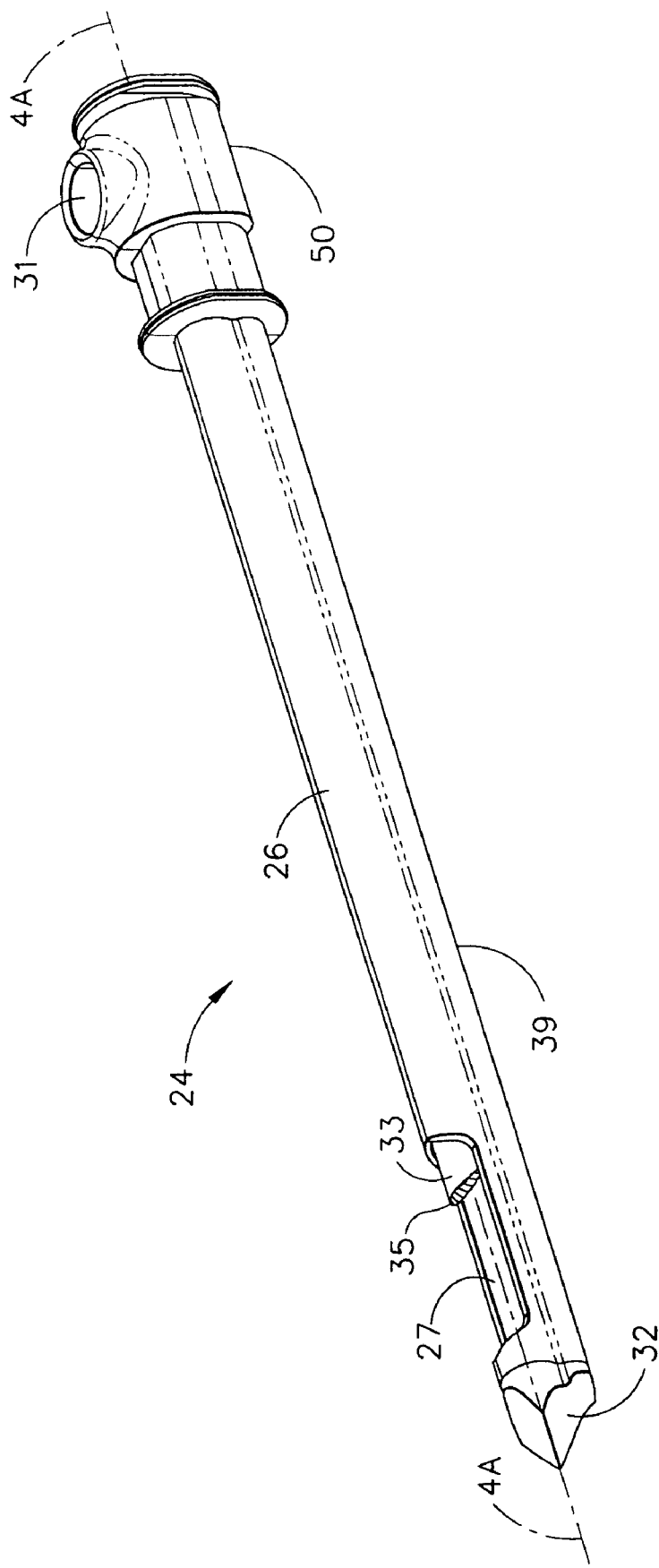
FIG. 2 presents a perspective view of the probe portion of the device illustrated in FIG. 1.
Figure 3:
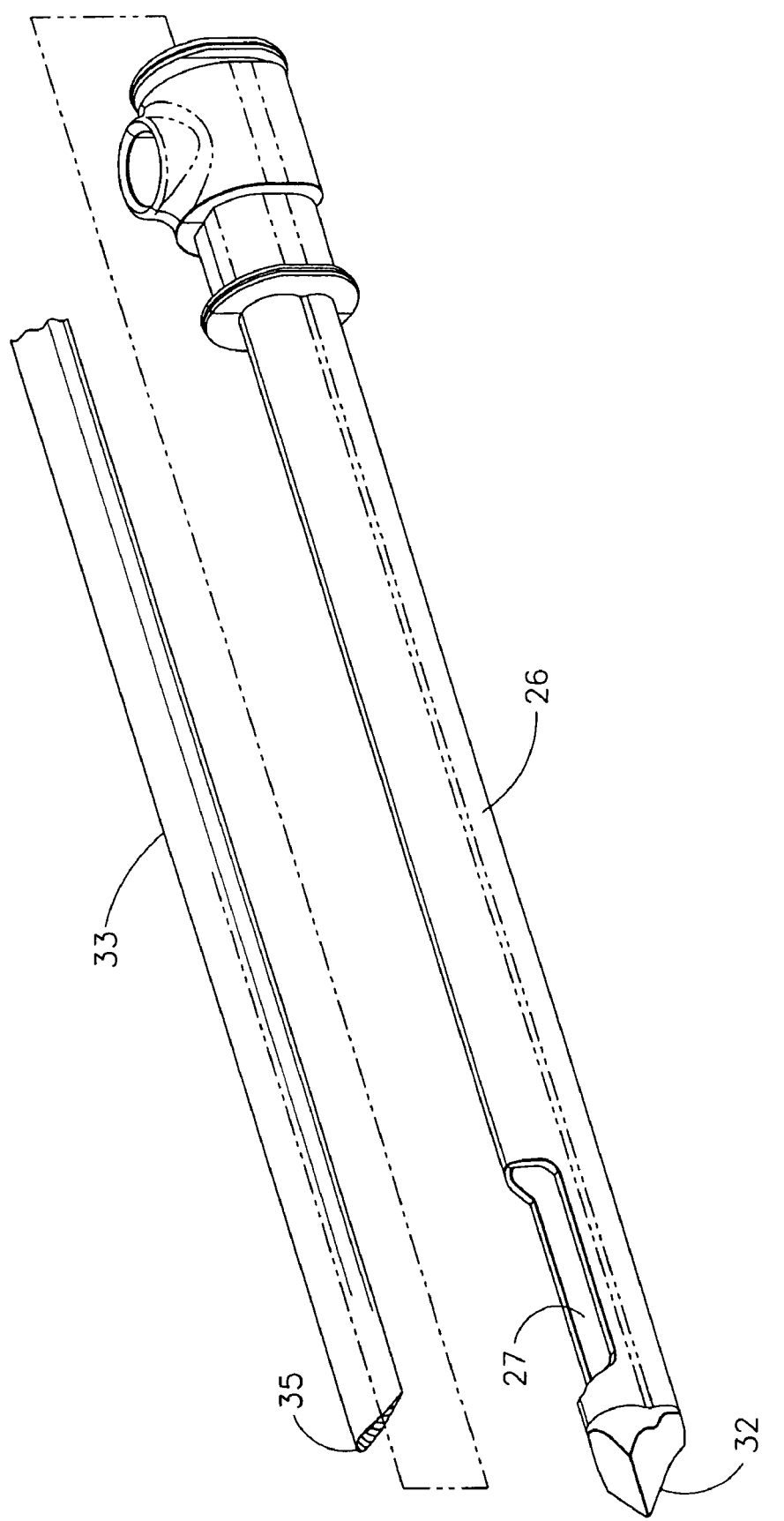
FIG. 3 presents an exploded perspective view of the probe of FIG. 2 and associated cutter.
Figure 4:
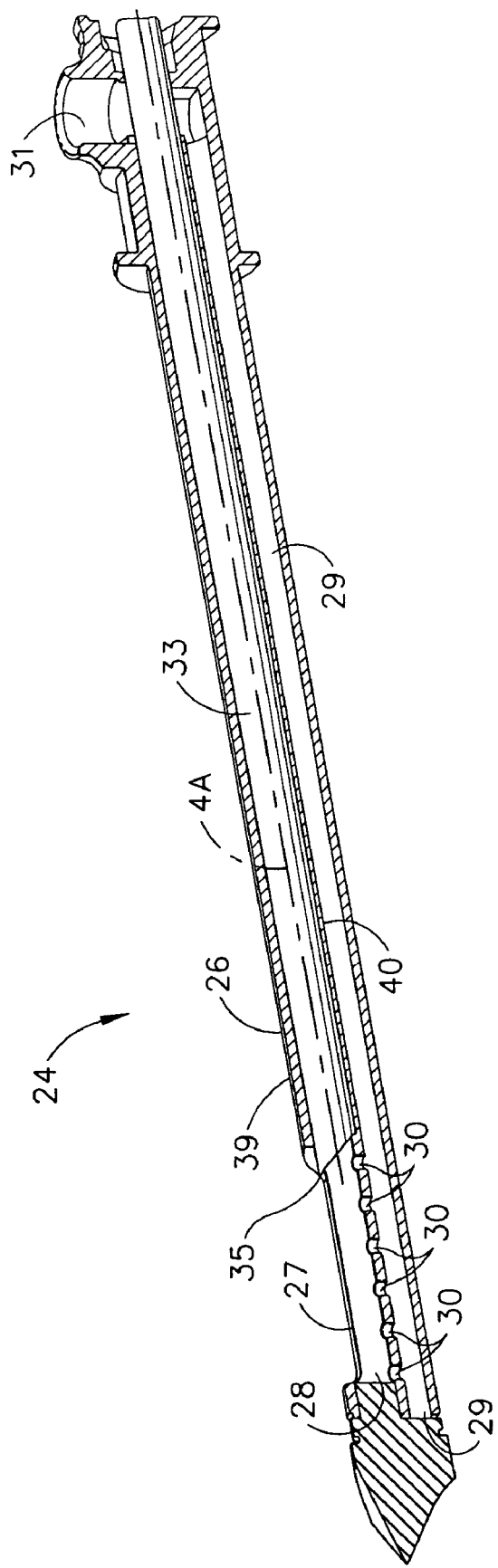
FIG. 4 presents a perspective cross-sectional view of the probe illustrated in FIG. 2 taken along line 4A-4A.

Referring now to FIGS. 2-4, in the exemplary version shown, device 20 includes a probe 24 having a probe shaft 26 having a proximal end and a distal end. The probe shaft 26 has receiving aperture 27 through the outer wall 39, which may be positioned near the distal end of the probe 24 as shown. In the version shown, the receiving aperture 27 has an oval shape, but the receiving aperture may have any shape suitable to permit effective vacuum aspiration of tissue as will be further described herein. The distal portion, or the entire perimeter, of the receiving aperture 27 may be bounded by a beveled or sharpened edge at outer wall 39. Such a beveled or sharpened edge may be included and/or situated to cooperate in scissors-fashion with an internal cutter (to be described below) to facilitate the severing of tissue.

In the exemplary version shown, probe 24 further includes cutter lumen 28 extending axially through the probe 24, configured to house and permit axial movement of a cutter 33 therethrough. Cutter lumen 28 may be formed in part by the outer wall 39 of the probe shaft 26, and in part by an inner wall 40 positioned within the probe 24.

Still referring to FIGS. 2-4, in the exemplary version shown, probe 24 includes vacuum lumen 29 through probe shaft 26. Inner wall 40 is provided with one or more vacuum ports 30. Vacuum ports 30 may include, for example, one or a plurality of holes suitably sized and positioned to allow the passage of air or other fluid therethrough. Vacuum ports 30 may be positioned such that vacuum may be transmitted through vacuum lumen 29, through vacuum ports 30, and into cutter lumen 28. In the illustrated version, vacuum lumen 29 is in fluid communication with a vacuum source port 31, where vacuum source port 31 may be connected to any suitable vacuum source including, for example, vacuum assembly 60 (shown in FIG. 14).

In the exemplary version, probe 24 terminates with probe tip 32, which is suitably shaped and suitably sharp so as to enable insertion of probe 24 into tissue and toward a target tissue mass without the necessity of a prior incision to establish a path for the probe to the target tissue mass. It will be appreciated that probe tip 32 may have any suitable piercing and/or cutting shape effective for piercing tissue to create a passage for the probe through tissue, and toward a target tissue mass.

Figure 5:
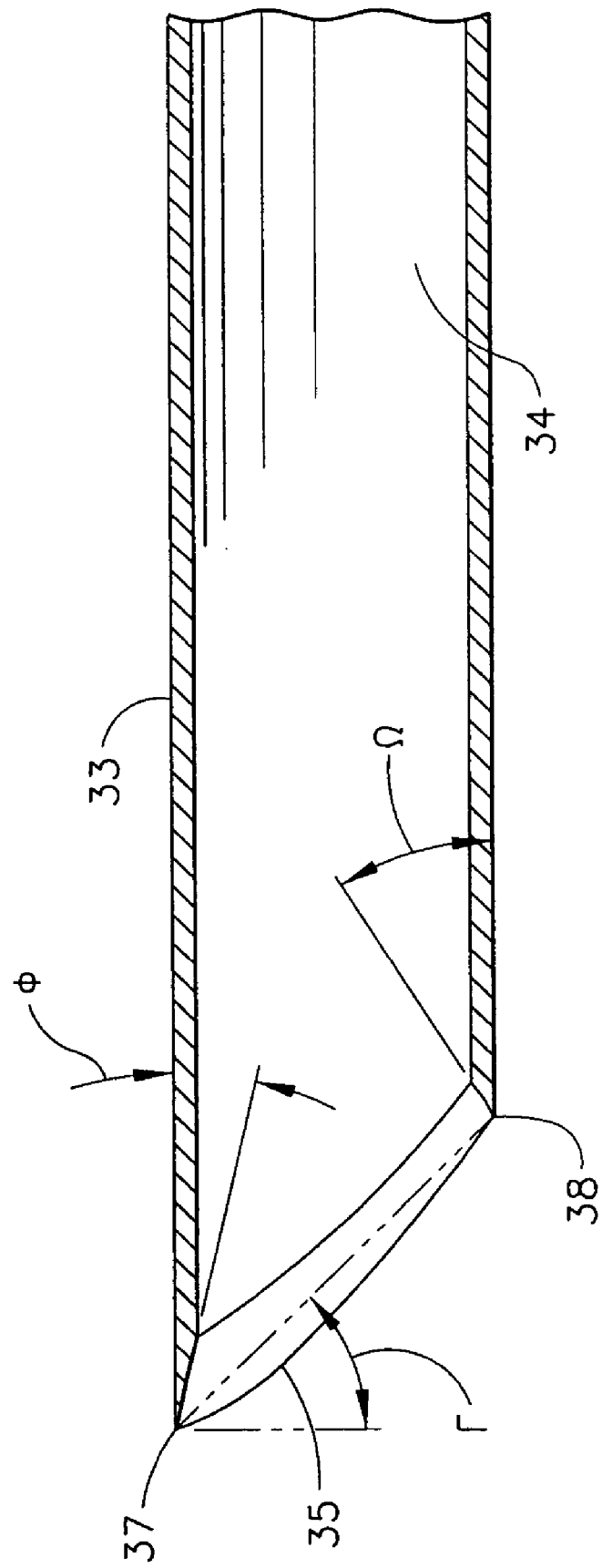
FIG. 5 presents a longitudinal cross-sectional view of the distal portion of the cutter illustrated in FIG. 3.
Figure 6:
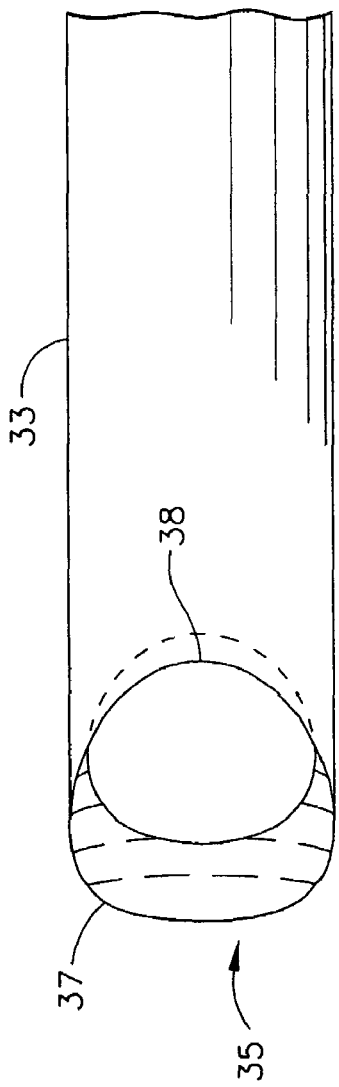
FIG. 6 presents a perspective view of the distal portion of the cutter illustrated in FIG. 3.
Figure 7:
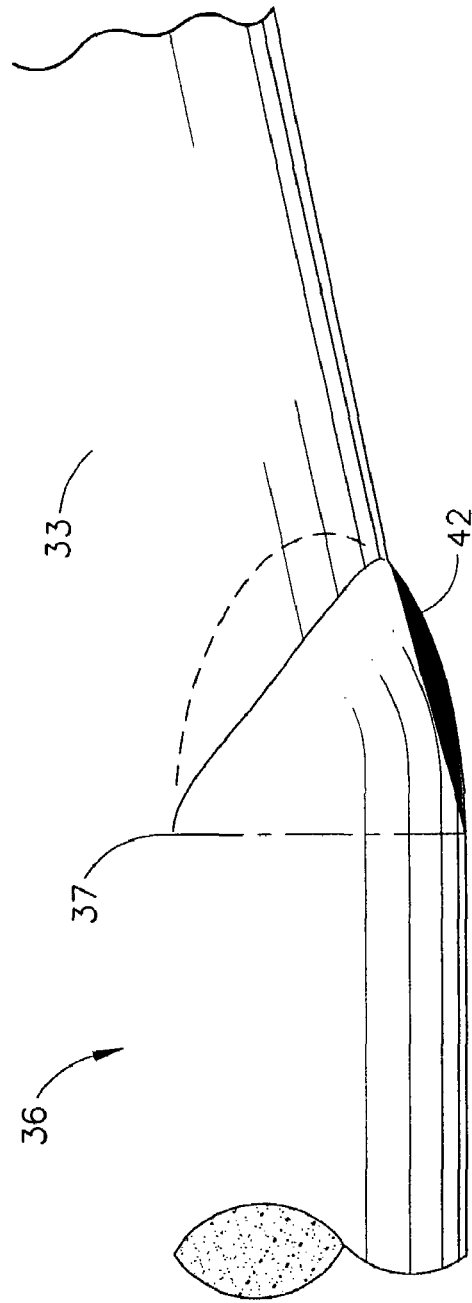
FIG. 7 presents a perspective view of the distal portion of the cutter of FIG. 3 with a grinder inserted into the distal tip of the cutter, illustrating an exemplary method of forming the cutting tip.
Figure 8:
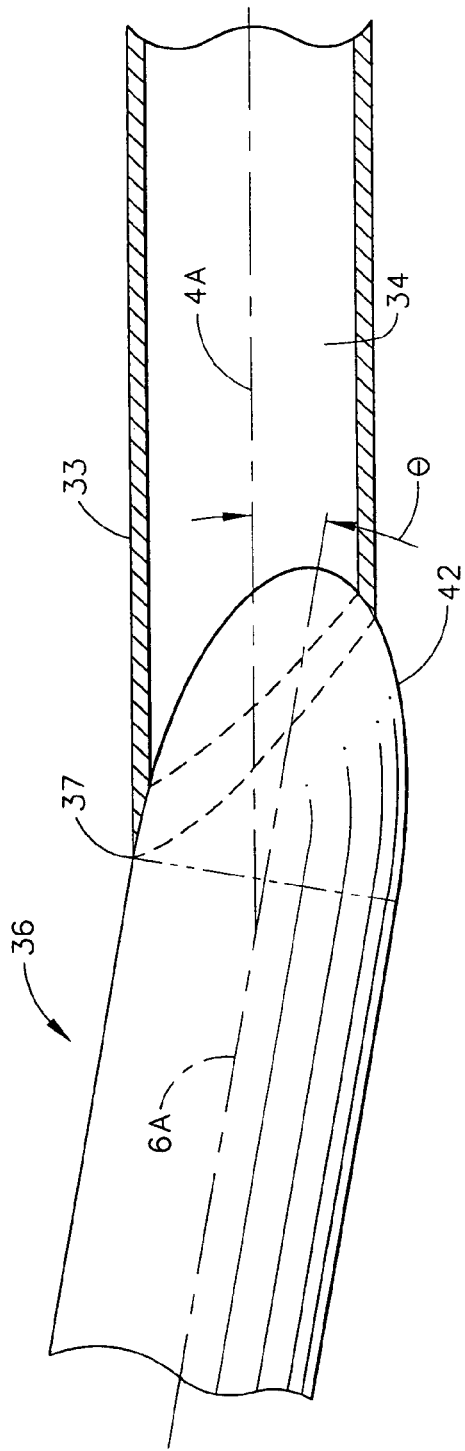
FIG. 8 presents a longitudinal cross-sectional view of the distal portion of the cutter of FIG. 3, shown with a grinder inserted into the cutter, illustrating an exemplary method of forming the cutting tip.
Figure 9:
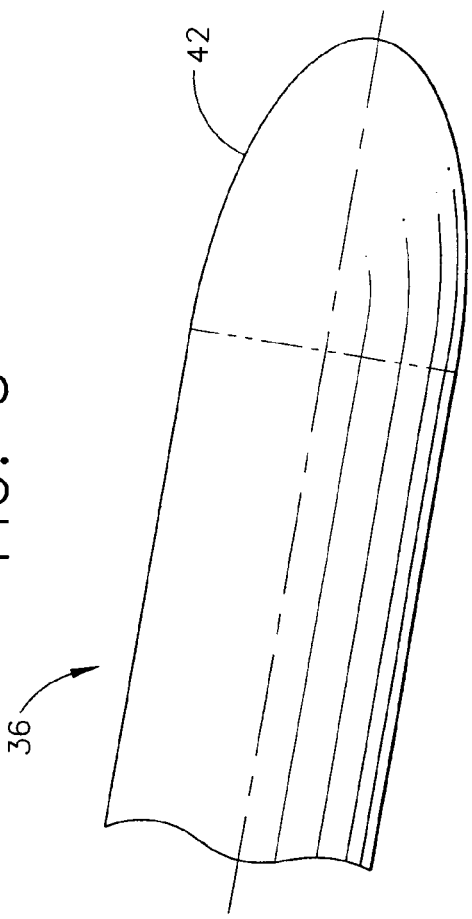
FIG. 9 presents a side perspective view of the grinder of FIG. 8.

In the exemplary version shown, cutter 33 is formed from hollow tube stock, which forms tissue lumen 34 (see FIG. 5). Cutter 33 may move longitudinally distally and proximally within cutter lumen 28 such that its cutting tip 35 may advance forwardly past receiving aperture 27, thereby closing receiving aperture 27, or retract rearwardly, thereby opening receiving aperture 27.

In the exemplary version, cutter 33 is provided with a cutting tip 35 at its distal end. Referring to FIGS. 5-8, cutting tip 35 has a cutting edge 37. Referring to FIG. 5, the angle $\Gamma$ is about 45° in the exemplary version depicted. However, the cutting tip may be formed in other versions wherein the angle $\Gamma$ (formed by a line connecting the most distal extent of cutting edge 37 and the most proximal extent of receding edge 38, and a line perpendicular to the longitudinal axis of the cutter as illustrated in FIG. 5), is from about 30° to about 60°, from about 40° to about 60°, from about 45° to about 60°, from about 45° to about 55°, or from about 45° to about 50°, or alternatively, about 50°, about 55° or about 60°. Providing a beveled or angled cutting tip 35 as shown in the illustrated versions results in a curved cutting edge 37 that has a distal-most point, and curves rearwardly on either side of the distal-most point.

Referring to FIGS. 5-9, it can be seen that the cutting tip 35, including the cutting edge 37, may be formed and/or sharpened by use of a suitably shaped rotating grinder 36. In the exemplary version of cutter 33 and the exemplary method of forming and/or sharpening illustrated, rotating grinder 36 has a semi-ellipsoid shape 42 at its distal end and a diameter that is larger than the diameter of the tube forming cutter 33. Alternatively, the grinder may have a hemispherical, hemispheroid, circular semi-paraboloid or other substantially convex distal end shape 42, at least at that portion of its surface (grinding surface) where it will contact and grind cutting edge 37 of cutter 33. Utilizing a grinder having a convex shaped grinding surface to form and sharpen cutting edge 37 provides for a cutting edge 37 having a concave grind, providing a thin and very sharp cutting edge.

Alternatively, the grinding surface of the grinder used may have a conical or cylindrical shape, if a cutting edge having a concave grind is not desired or deemed necessary.

Another technique for producing a thin, sharp cutting edge resides in control and manipulation of the sharpening angle $\Phi$ for cutting edge 37 (see FIG. 5). In the exemplary version shown, sharpening angle $\Phi$ is about 14°. Alternatively, in other versions sharpening angle $\Phi$ of cutting edge 37 may be from about 10° to about 14°, from about 10° to about 15°, from about 10° to about 20°, or from about 10° to about 25°, or alternatively, about 10°, about 11°, about 12°, about 13°, about 14° or about 15°. Referring to the example illustrated in FIGS. 5-8, it can be appreciated that sharpening angle $\Phi$ may be adjusted by adjusting the angle $\theta$ at which the grinder is brought into contact with the distal end of cutter 33. It will be appreciated also that the sharpening angle of the cutting edge can be affected by the diameter of the grinder and the particular shape and/or angle of the grinding surface.

The sharpening angle and extent of concavity of grind for cutting edge 37 may be adjusted to strike a desired balance between edge thinness and sharpness and tissue cutting effectiveness, and lateral edge strength and edge durability, as may be suitable for the use to which the device may be put. The contemplated use for the exemplary versions illustrated herein is taking multiple breast tissue biopsy samples during a single probe insertion, but is not necessarily limited to that application.

It will be appreciated that the shaping and sharpening of cutting edge 37 of cutter 33 may be of particular concern when a predominantly translational (e.g., substantially non-rotating) cutting stroke is provided by the associated device.

In this circumstance, a thin, very sharp edge may be more desirable for cutting certain types of soft tissue or organ tissue, which might in some circumstances be elastic and evasive to substantially translational advancement of a cutting edge through a protruding portion thereof.

If the cutter 33 is used in conjunction with a probe 24 with a receiving aperture 27 defined in part by a sharpened edge to cooperate in scissors-fashion with cutting edge 37, a very thin, extremely sharp cutting edge 37 may in certain circumstances be deemed of lesser importance, or may be deemed undesirable, if more lateral edge strength is deemed desirable.

The shape and edge sharpness of receding edge 38 in the exemplary version shown in the figures may be of lesser concern, because for the substantially translating cutter motion provided in the exemplary examples described herein, receding edge 38 may not be substantially involved in cutting tissue. However, it also will be appreciated that a grinder having an ellipsoid, paraboloid, spherical or other convex-shaped grinding surface, the grinder of larger diameter than that of the outer diameter of the tube stock from which cutter 33 is formed, may be brought into contact with the tube stock wherein, with reference to FIG. 8, axes 4A and 6A are collinear and angle θ is zero, so as to form no distinguishably leading or receding edges on cutter 33. Rather, with reference to FIG. 5, angle Γ may be zero and the entire circumference of the tube end may be given a uniform and squared-off cutting edge having a concave grind, such that the resulting cutter might be rotated during a cutting stroke to enhance tissue cutting effectiveness via slicing action, or alternatively, if the device provides only substantially translational cutting motion during actuation, to allow for rotation of a fresh cutting edge into a position proximate to the receiving aperture of the probe during the procedure, in a suitably configured device.

The illustrated and described version of cutter 33 is contemplated as formed from, by way of example, stainless steel. For example, the cutter may be AISI 17-7 PH or type 631 (UNS17700) stainless steel, condition CH900, suitably hardened to hold a cutting edge. Other stainless steels may be suitable, including but not limited to, for example, type 304, type 316 or type 420 stainless steel or other martensitic stainless steel. However, a suitable cutter also may be formed from titanium and/or another metal or metal alloy, including a non-ferrous metal or alloy, which might be selected, for example, so as to be either invisible, or to cause minimal or no distorting effects, when used in conjunction with imaging and guiding techniques and equipment, such as a plastic or a ceramic material, or any other suitable material, including a combination of materials, that provides for shaping and sharpening of an edge of substantial razor-sharpness and sufficient strength and durability for the application contemplated.

In the exemplary version depicted, cutter 33 may be formed, for example, from tube stock having, for example, an inner diameter of about 0.085" and an outer diameter of about 0.1025"; or an inner diameter of about 0.063" and an outer diameter of about 0.072", or any other suitable combination of inner and outer diameters.

For example, referring to FIGS. 5-9, for a cutter 33 having an inner diameter of about 0.085" and an outer diameter of about 0.1025", an angled cutting tip 35 and a cutting edge 37 having a concave grind may be formed by a rotating grinder 36 having a semi-ellipsoid end shape 42 and a diameter of about 0.1128", semi-minor axis for the ellipsoid end shape 42 of about 0.0564", and a semi-major axis for the ellipsoid end shape 42 of about 0.1350". The grinder 36 may be applied to form and sharpen cutter 33 at an angle θ (see FIG. 8) of about 10 degrees, where the forwardmost extent of the cutting edge 37 terminates where the full diameter of the grinder 36 begins, marking the intersection of the semi-minor axis of the semi-ellipsoid end shape 42.

By way of further example, referring to FIGS. 5-9, for a cutter 33 having an inner diameter of about 0.063" and an outer diameter of about 0.072", an angled cutting tip 35 and a cutting edge 37 having a concave grind may be formed by a rotating grinder 36 having a semi-ellipsoid end shape 42 and a diameter of about 0.080", semi-minor axis for the ellipsoid end shape 42 of about 0.040", and a semi-major axis for the ellipsoid shape 42 of about 0.094". The grinder 36 may be applied to form and sharpen cutter 33 at an angle θ (see FIG. 8) of about 10 degrees, where the forwardmost extent of the cutting edge 37 terminates where the full diameter of the grinder 36 begins, marking the intersection of the semi-minor axis of the semi-ellipsoid end shape 42.

The grinder 36 may be made of, or tipped or coated with, any suitable fine grinding material, including but not limited to carbide or ceramic material. The grinder may be run at relatively high rotational speeds suitable for producing surgically sharp cutting edges on the selected material, and the grinder and/or cutter tube stock may be cooled using suitable methods during grinding as may be desired to prevent undesirable heating of the cutter tube stock during cutting edge formation and sharpening.

The foregoing are only examples and it will be appreciated that cutters of other dimensions and materials having angled cutting tips and cutting edges with concave grinds may be produced using the techniques described above.

Referring back to FIGS. 2-5, the exemplary version of the probe 24 and cutter 33 combination may be used as follows. Following identification of a target tissue mass within a patient, such as a suspected mass within breast tissue, the user may, using suitable immobilization equipment and suitable imaging and/or guidance techniques and equipment, insert probe 24 into and through the skin and tissue, until receiving aperture 27 is within or adjacent to the suspected tissue mass. During insertion, cutter 33 may be held in a forward position so that receiving aperture 27 is closed. When receiving aperture 27 is in the desired location, using a suitable actuating device and/or other equipment associated with the probe, the user may cause cutter 33 to retract proximally so as to open receiving aperture 27 and place cutter 33 into a position ready for cutting. Contemporaneously or thereafter the user may cause (manually or by operating any suitable associated device or equipment) a vacuum to be applied via, for example, vacuum source port 31. This vacuum can be transmitted to cutter lumen 28 via vacuum lumen 29 and vacuum ports 30, or any other suitable porting or ducting structures or passages, which will cause tissue to be drawn into cutter lumen 28 through receiving aperture 27. Then, cutter 33 can be advanced forwardly, in substantially translational motion, so that its cutting edge 37 will contact and sever the tissue drawn into the cutter lumen. As cutter 33 advances, the tissue severed by cutting edge 37 is captured within tissue lumen 34 in cutter 33. As noted above, the distal portion of the edge of receiving aperture 27 may be sharpened so as to cooperate in scissors-fashion with cutter 33 as it advances, to facilitate a final separation or snipping of the tissue being severed during the cutting stroke. The severed tissue may then be collected from the tissue lumen 34 by any suitable mechanism. It will be appreciated that a variety of devices and mechanisms may be designed and manufactured to be associated with probe 24 and cutter 33 to effectuate the steps described above.

In another version, a cutter may formed from a semi-circular, elliptical or other shaped hollow member, as an alternative to a circular tube. Alternatively, a cutter might be formed from a member of a minimal size necessary and sufficient to support and drive a cutting edge, for example, a longitudinal member having an open semi-circular or semi-elliptical transverse cross section. Reducing the size of a cutter will permit reduction in size of an associated probe, which will reduce patient discomfort and tissue trauma caused by a procedure. It will be appreciated, however, that a reduction in size of a cutter and probe combination results in a reduction in the amount of tissue that may be removed in a single cutting stroke, which may be undesirable, for example, if a more substantial tissue sample from a single cutting stroke is desired, or if the combination is to be used not only for tissue sampling purposes but also for therapeutic tissue excision purposes.

Figure 10:
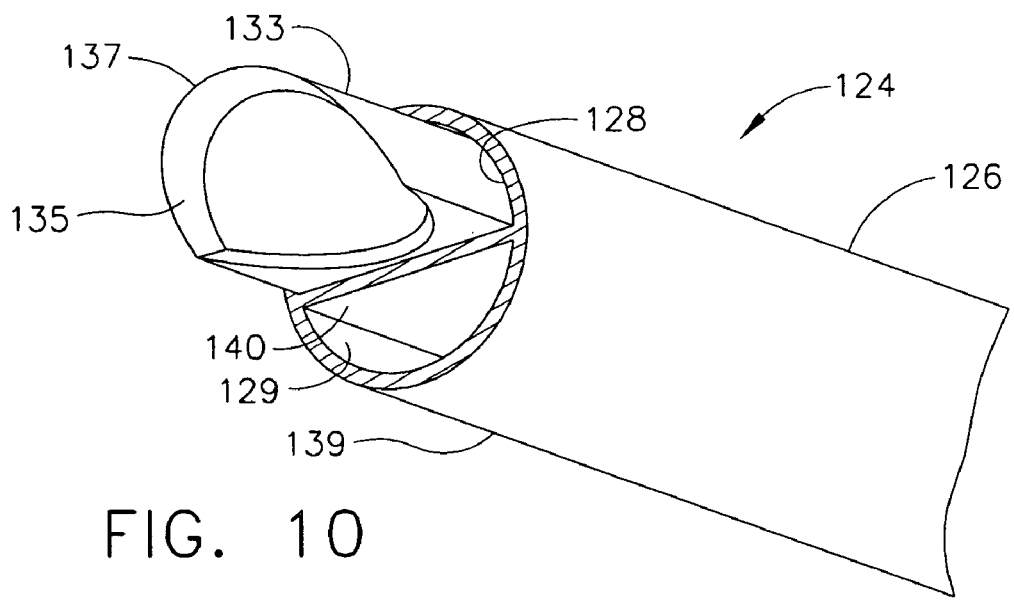
FIG. 10 presents a partial perspective and transverse cross-sectional view of an alternate version of a cutter and an alternate probe shaft.

Referring to FIG. 10, an exemplary alternative version of a probe 124 (shown in perspective cross section, without a distal end or receiving aperture) is depicted including an arched or semi-circular cutter 133. In the illustrated exemplary version, the probe shaft 126 is circular or elliptical in cross section and is divided by an inner wall 140 into a cutter lumen 128 and a vacuum lumen 129. The vacuum lumen 129 may be used to transmit vacuum from a vacuum source (not shown) to a receiving aperture (not shown) for example, in the manner described for the alternative version above. The cutter lumen 128 may be, for example, semi-circular in transverse cross section or any other suitable transverse cross sectional shape that houses and provides for the longitudinal movement of a matching cutter 133. The inner wall 140 at least partially defining the cutter lumen 128 may be provided with vacuum ports (not shown) as described above for the alternate versions herein. Cutter 133 may be provided with cutting tip 135 having a cutting edge 137. Cutting tip 135 may be formed by a grinder, such as a grinder 36 (FIG. 9), as discussed above. Providing, as in the example shown in FIG. 10, a semi-circular transverse cross sectional shape for cutter 133 may allow for reduction of the overall cross-sectional size of the probe 124 thereby reducing the discomfort to the patient and trauma to the tissue caused by a procedure in which the probe is used.

Figure 11:
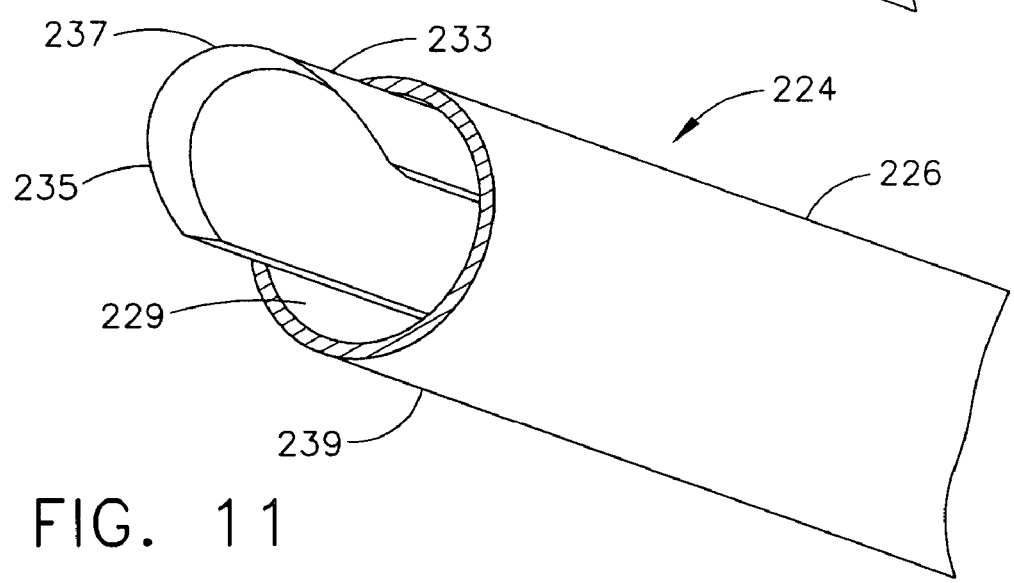
FIG. 11 presents a partial perspective and transverse cross-sectional view of an alternate version of a cutter and an alternate probe shaft.
Figure 12:
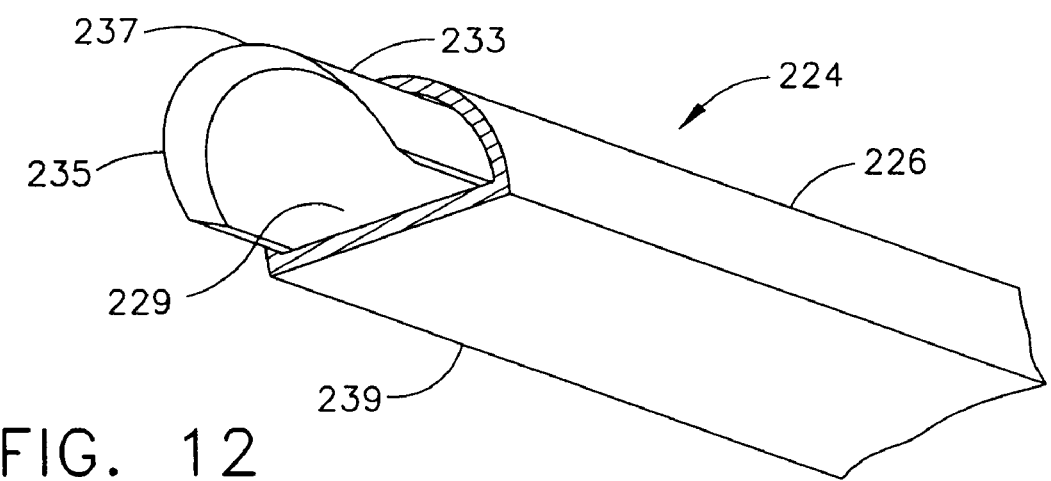
FIG. 12 presents a partial perspective and transverse cross-sectional view of an alternate version of a cutter and an alternate probe shaft.
Figure 13:
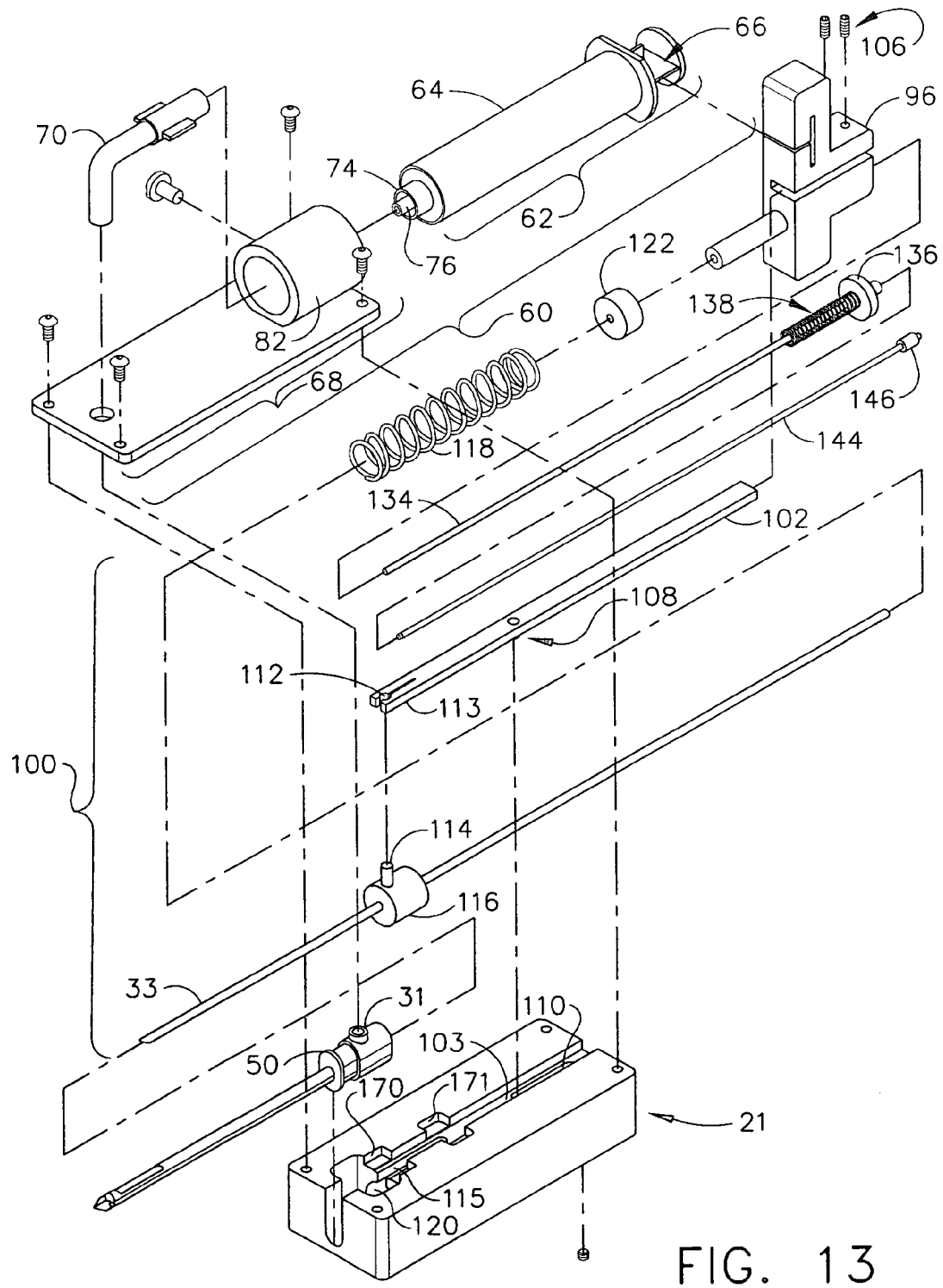
FIG. 13 presents an exploded perspective view of the device shown in FIG. 1.

Referring to FIGS. 11-12, additional alternative versions of a probe 224 are depicted, including a cutter 233 having a semicircular, semi-elliptical or arched transverse cross sectional shape. In one version, the probe shaft 226 is circular or elliptical in transverse cross-sectional shape and the cutter 233 is correspondingly semi-circular or semi-elliptical in cross-sectional shape and is adapted to fit and move axially within the single lumen 229. The cutter 233 may be associated with a structure integral thereto, or integral with the probe outer wall 239, such as a track or guide (not shown), to cause cutter 233 to be held and to move axially in adjacent fitting contact to the outer wall 339 as shown. In the absence of an inner wall defining separate vacuum and cutter lumens within probe 224, vacuum may be applied and transmitted by lumen 229 or by a lumen within a hollow shaft or other structure (not shown) within or about probe 224 to a receiving aperture (not shown) in probe 224 by a suitable configuration and sealing arrangement within an instrument body associated with probe 224.

It will be noted, however, that in all alternative versions of cutter 33, 133, and 233 or other versions not specifically illustrated, a cutting edge such as cutting edge 37, 137, 237, may be imparted with sharpness and cutting ability by forming/sharpening techniques and a grinder such as discussed above, so as to be suitable and effective in severing tissue in a substantially translational cutting stroke. For example, as discussed, if a grinder having a convex grinding surface is used to shape or sharpen cutting edge 37, 137, 237, a cutting edge having a concave grind can be produced that is effective for cutting tissue in a substantially translational stroke of the cutter.

Referring back to FIG. 1, versions of a device such as device 20 may be operably configured to provide for severing and collecting multiple tissue samples and/or excising tissue, with a single insertion of a probe 24. A device such as device 20 may be operably configured to be operated and used without an external vacuum or power source. Provided in versions discussed herein is a substantially non-rotational cutting mechanism that may be configured to provide the user with an efficient, simple, and versatile tissue removal instrument for performing a variety of minimally invasive internal tissue removal procedures.

Referring to FIGS. 1-2 and 13-15, an exemplary version of such a device 20 is depicted. Device 20 includes probe 24 affixed within or to body 21, vacuum assembly 60 held by body 21, cutter driver mechanism 100 held by body 21, and actuator 96.

In the exemplary version depicted, vacuum assembly 60 includes a syringe 62 having syringe body 64 and an actuating member such as plunger 66 having plunger tip 67, for creating a vacuum. The size and/or proportions of syringe 62 may be selected such that approximately 5 cc of space is created or displaced therein, respectively, during retraction or advancement, respectively, of plunger 66 as will be described further below. It will be appreciated that a syringe (as that term may be typically understood, such as, for example, a hypodermic syringe) is suitable but not necessary. Rather, any suitable aspirator, cylindrical or otherwise, or other mechanism that creates vacuum upon the movement of an actuating member thereof, may be utilized. Nozzle 76 of syringe 62 is connected in a substantially fluid-tight manner to vacuum source port 31 of probe 24, via vacuum tube 70 or any other suitable conduit structure. Syringe body 64 may be affixed to body 21 via a holder 82. Thus disposed, syringe 62 or other suitable aspirator can constitute a vacuum source for the device.

As previously described above, in the exemplary versions depicted cutter 33 rides longitudinally within probe 24. Cutter 33 extends from its distal end within probe 24, proximally through body 21, terminating with an open proximal portion that may slide longitudinally within actuator 96 as may be seen in FIG. 14. Spring collar 116 is affixed about cutter 33 so as move integrally therewith and limit the axial movement thereof. As may be seen in FIG. 14, firing spring 118 is substantially coaxial with cutter 33 and is held in compression against spring collar 116 at its distal end and against rear block 122 at its proximal end. Rear block 122 is affixed within body 21. Thus, it can be appreciated that firing spring 118 acts to urge cutter 33 forward relative to body 21, via spring collar 116. In a pre-deployment position, spring collar 116 rests against a forward stop structure, or alternatively, probe boss 50, within body 21 under urging of firing spring 118. Spring collar 116 has projecting therefrom an integral firing pin 114. As spring collar 116 moves longitudinally within body 21, firing pin 114 moves longitudinally within firing pin track 115 integral with body 21.

In the exemplary version depicted, the proximal end of plunger 66 of syringe 62 is integrally affixed to or within actuator 96 by any suitable mechanism, such as but not limited to mating/fitting geometry or set screws. Thus, it can be appreciated that proximal and distal motion of actuator 96 will effect substantially corresponding, parallel and coextensive proximal and distal motion of plunger 66, relative to body 21. Also integrally affixed to or within actuator 96 is the proximal portion of retraction member 102. Retraction member 102 rides longitudinally within retraction track 103 incorporated into body 21, and also moves substantially correspondingly, in parallel and coextensively in proximal and distal directions along with plunger 66, with movement of actuator 96. Retraction member 102 has integral limiting pin 108 extending downwardly therefrom and into limiting track 110 within body 21. As retraction member 108 is moved rearwardly or forwardly relative to body 21, its rearward and forward motion is checked by interaction of limiting pin 108 with limiting track 110.

In the exemplary version depicted, retraction member 102 has at its distal end a nock 112 formed by two flexible extensions 113. Nock 112 is adapted to snapably engage and disengage firing pin 114 of spring collar 116, enabled by the outward flexing of the flexible extensions 113 as may be appreciated from FIG. 13. As noted, retraction member 102 rides longitudinally within retraction track 103. The width and sides of retraction track 103 are adapted so as to snugly fit about retraction member 102 or vice versa, and thereby prevent outward flexing of the flexible extensions 113 forming nock 112. However, retraction track 103 includes engagement cavity 170 and disengagement cavity 171. When nock 112 of retraction member 102 is moved to either engagement cavity 170 or disengagement cavity 171 via distal or proximal longitudinal movement of retraction member 102 within retraction track 103, the flexible extensions 113 of nock 112 may flex outwardly laterally, which will permit engagement or disengagement of nock 112 with firing pin 114, as will be described below.

In the exemplary version depicted, device 20 also may include a removable sample collection assembly inserted into the open proximal end of, and residing within, cutter 33. Sample collection assembly 130 may include collection tube 134 and ejector rod 144, both of which are coaxial with cutter 33 when inserted therein. Collection tube 134 is open at both ends, and the proximal end has collection tube knob 136 integrally affixed thereto. Collection tube 134 may be formed of a suitable plastic such as polyethylene or other suitable material, and have a wall thickness of about 0.007" to 0.011"; it will be appreciated that a thinner collection tube wall will ease movement past, and collection of, tissue samples within the cutter 33 as will be described below, but that a collection tube wall that is too thin may lack suitable strength and stiffness. Ejector rod 144 has ejector rod knob 146 integrally affixed at or near the proximal end thereof, and when ejector rod 144 is fully inserted into collection tube 134, ejector rod knob 146 rests against collection tube knob 136, and may rest within a recess in collection tube knob 136 as shown. Return spring 138 is situated on collection tube 134 distally adjacent to collection tube knob 136. In the exemplary version, collection tube 134 is of a length that is substantially equal to or greater than the length of cutter 33, such that by axial/longitudinal depression of collection tube knob 136 by the user in a distal direction, and resulting compression of return spring 138 against actuator 96, the distal end of collection tube 134 may be brought substantially proximate to the distal end of cutter 33. Ejector rod 144 is preferably of a length that is substantially equal to the length of collection tube 134 when fully inserted therein. In the exemplary version, ejector rod 144 is of a diameter such that it fits sufficiently snugly within the inside diameter of collection tube 134, such that vacuum applied by vacuum assembly 60 and transmitted into cutter lumen 28 will not draw ejector rod 144 in a forward direction within collection tube 134, rather than draw tissue into receiving aperture 27. At the same time, however, the fit must be loose enough so as to permit ejector rod 144 to slide rearwardly within collection tube 134 when urged by the contact and pressure of tissue and/or fluid entering the distal end of collection tube 134, as it is advanced by the user to collect severed tissue as will be described further below. Collection tube 134 is of a diameter such that it fits sufficiently snugly within the inside diameter of cutter 33, such that vacuum applied by vacuum assembly 60 and transmitted into cutter lumen 28 will not draw collection tube 134 together with ejector rod 144 in a forward direction within collection tube 134, rather than draw tissue into receiving aperture 27. At the same time, collection tube 134 must not fit within cutter 33 so snugly as to prevent movement therewithin at the urging of the user as will be described below.

Figure 16:
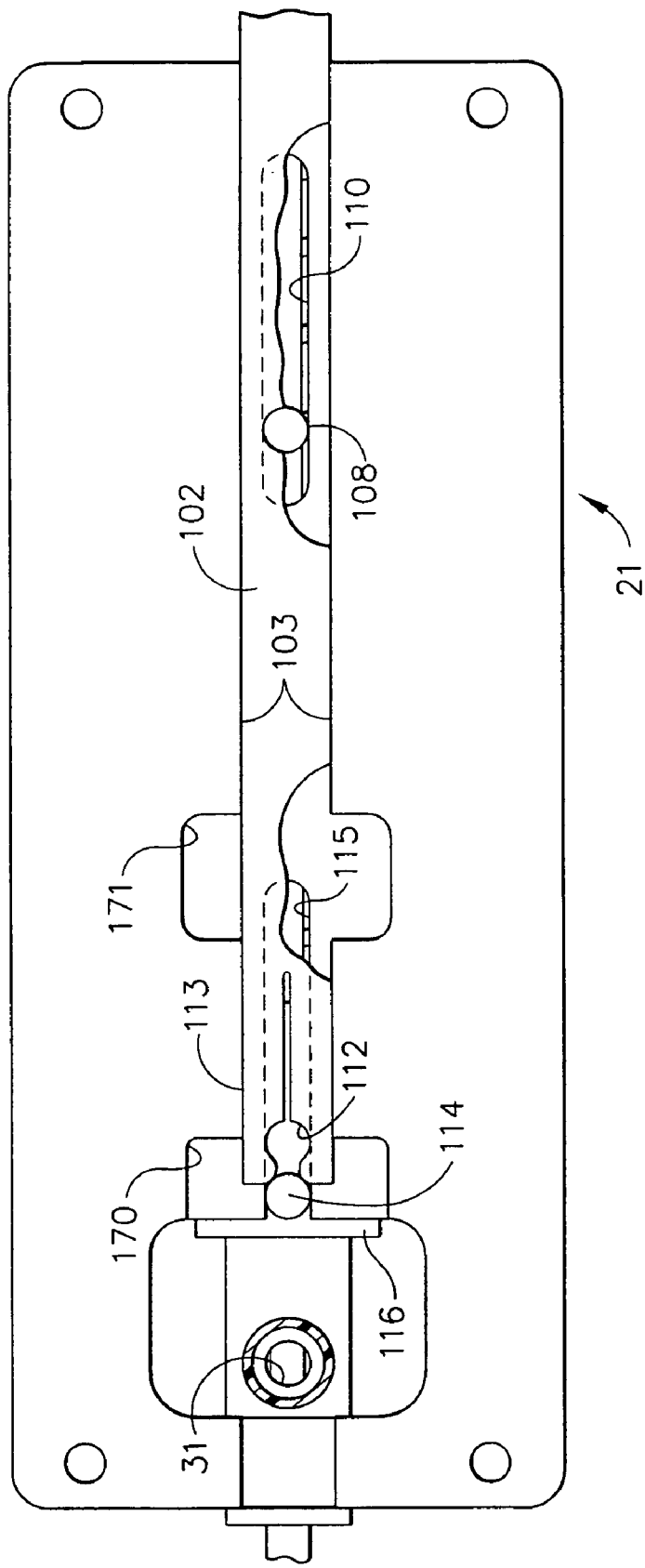
FIG. 16 presents a top sectional view of the body portion of the device as shown in FIG. 14.

FIGS. 14-16 depict the exemplary version of the device in a predeployment position. Cutter 33 is in its forwardmost position under urging of firing spring 118 acting against spring collar 116, and thus receiving aperture 27 of probe 24 is closed by cutter 33. Nock 112 of retraction member 102 is not engaged with firing pin 114, but is adjacent thereto (see FIG. 16). It can be seen in FIG. 14 that sufficient clearance exists between the tip 67 of plunger 66 and the inside distal limit of syringe body 64 to allow actuator 96 to be moved forward a distance sufficient to cause engagement of nock 112 of retraction member 102 with firing pin 114. It also can be seen in FIG. 14, that the flexible extensions 113 of nock 112 have clearance within engagement cavity 170 in which to move outwardly laterally and allow engagement of nock 112 with firing pin 114, upon urging of retraction member 102 in a distal direction. With the device in this position, probe 24 may be inserted into tissue, toward a target tissue mass.

Figure 17:
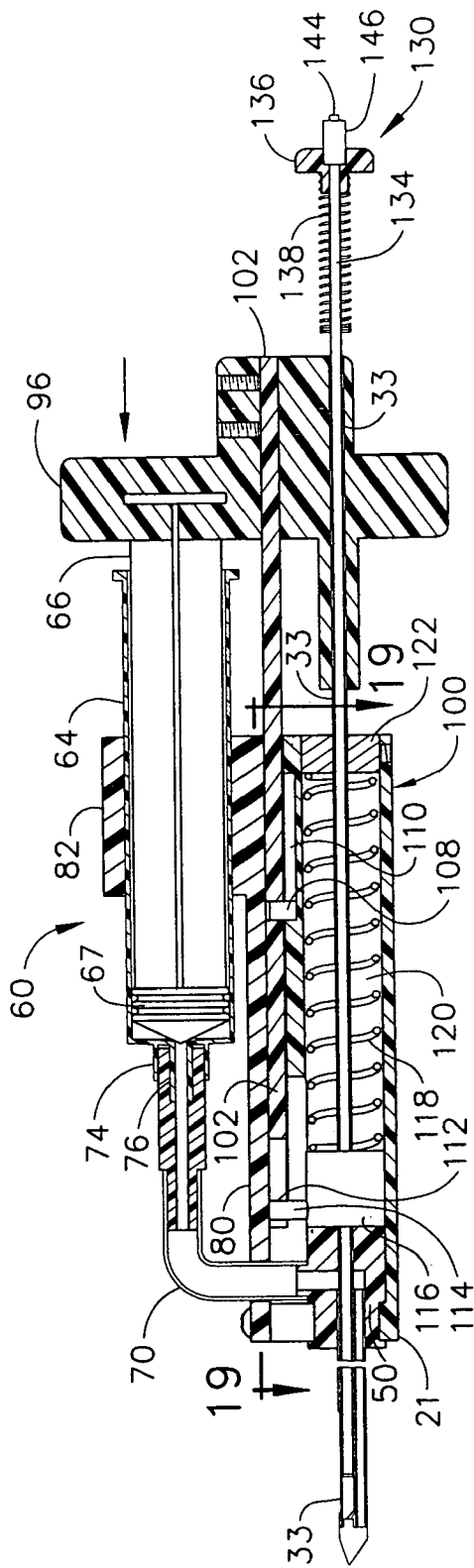
FIG. 17 presents a side longitudinal cross-sectional view of the device of FIG. 1, in an engaged position.
Figure 18:
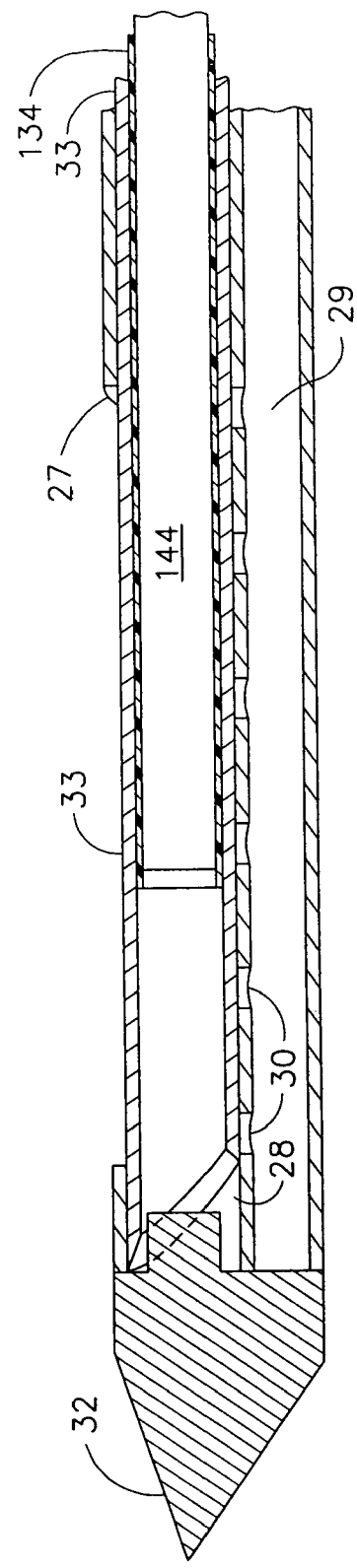
FIG. 18 presents a side longitudinal cross-sectional view of the probe as shown in FIG. 17.
Figure 19:
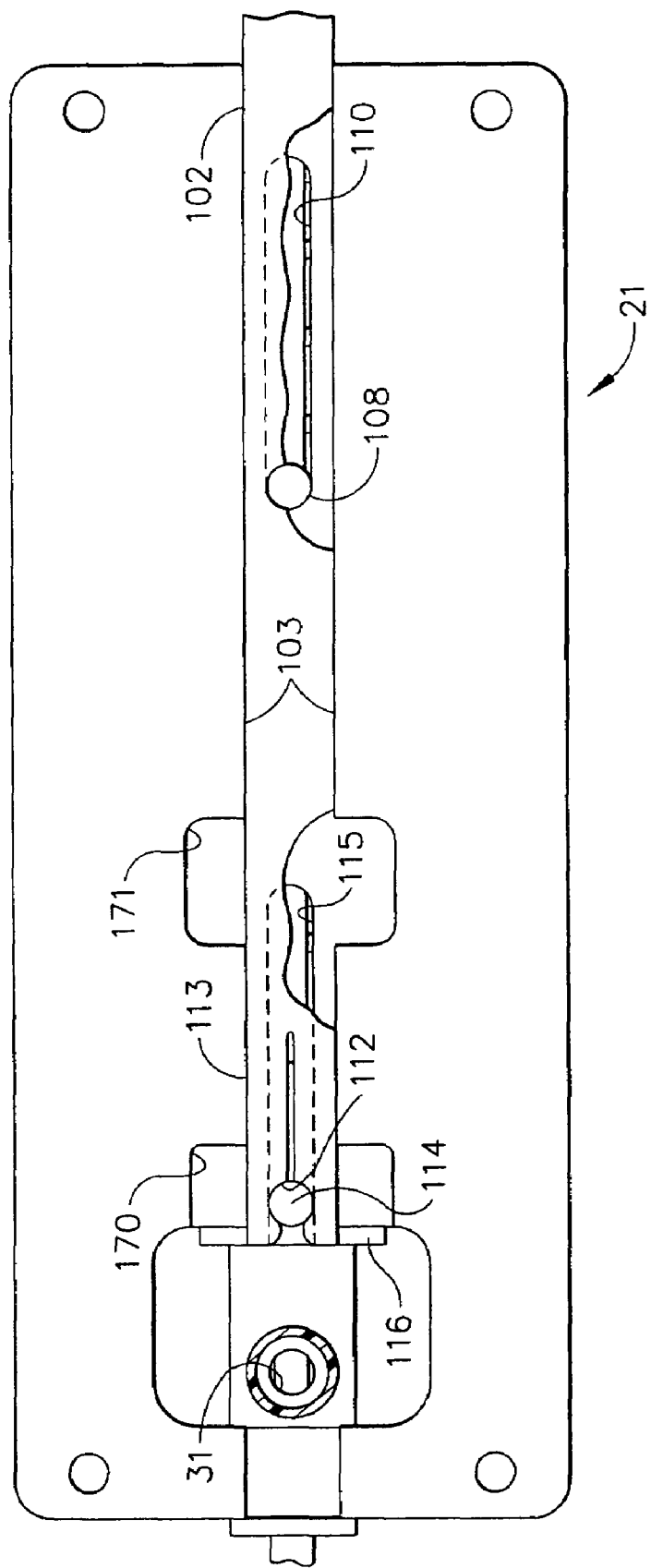
FIG. 19 presents a top sectional view of the body portion of the device as shown in FIG. 17.

FIGS. 17-19 depict the exemplary version of the device after the retraction member 102 has been engaged with the cutter 33 via engagement of nock 112 about firing pin 114. In order to move the components of the device into this position, the user may push or otherwise effect movement of actuator 96 in a forward direction relative to body 21. Because retraction member 102 is integral with actuator 96, forward movement of actuator 96 relative to body 21 effects corresponding forward movement of retraction member 102, and nock 112 is urged against firing pin 114. Advanced forwardly into engagement cavity 170, the flexible extensions 113 forming nock 112 are permitted to flex outwardly laterally within the clearance provided by engagement cavity 170, allowing nock 112 to open and snap onto and about firing pin 114, thereby grasping it. At the same time, forward movement of actuator 96 with respect to body 21 effects corresponding forward movement of plunger 66 with respect to syringe body 64, thereby expelling air or other fluids from syringe body 64, which may be vented or drained as necessary, for example, by a mechanism described below or by any other suitable mechanism. In this way the device is made ready for drawing in and cutting tissue. Forward motion of retraction member 102 is limited to a forwardmost extent by interaction of limiting pin 108 with track 110. As an alternative to insertion of probe 24 into tissue prior to engagement of the firing pin 114, probe 24 may be inserted into tissue and toward a target tissue mass after such engagement of firing pin 114.

Figure 20:
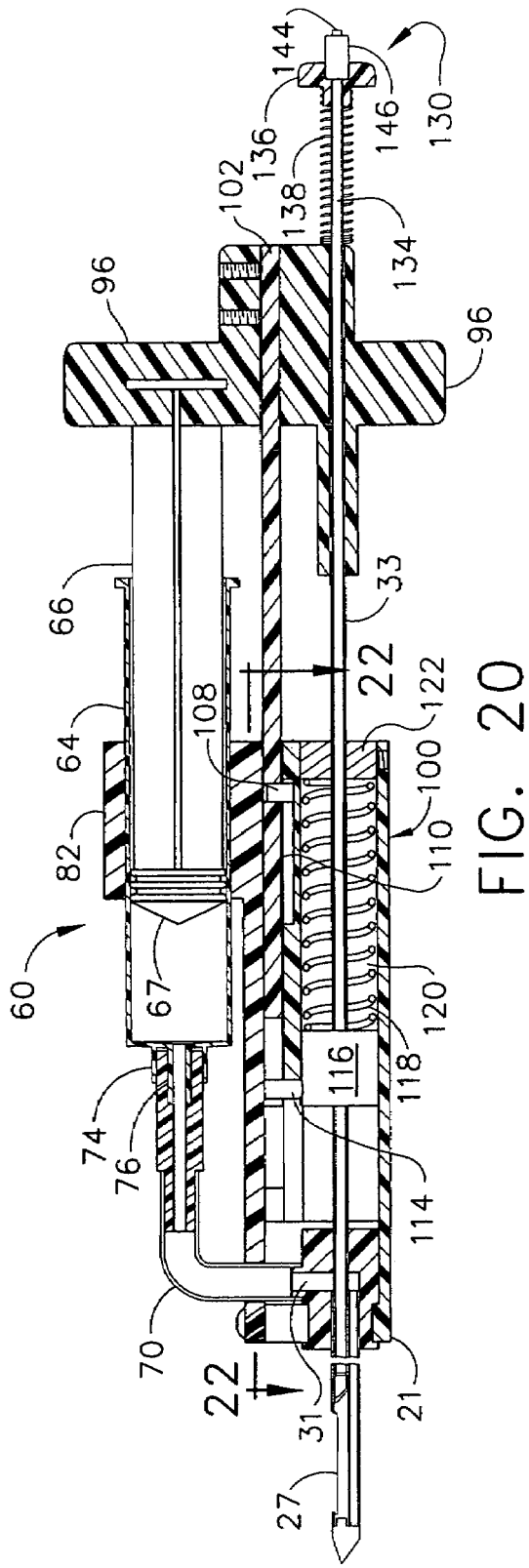
FIG. 20 presents a side longitudinal cross-sectional view of the device of FIG. 1, in a retracted position.
Figure 21:
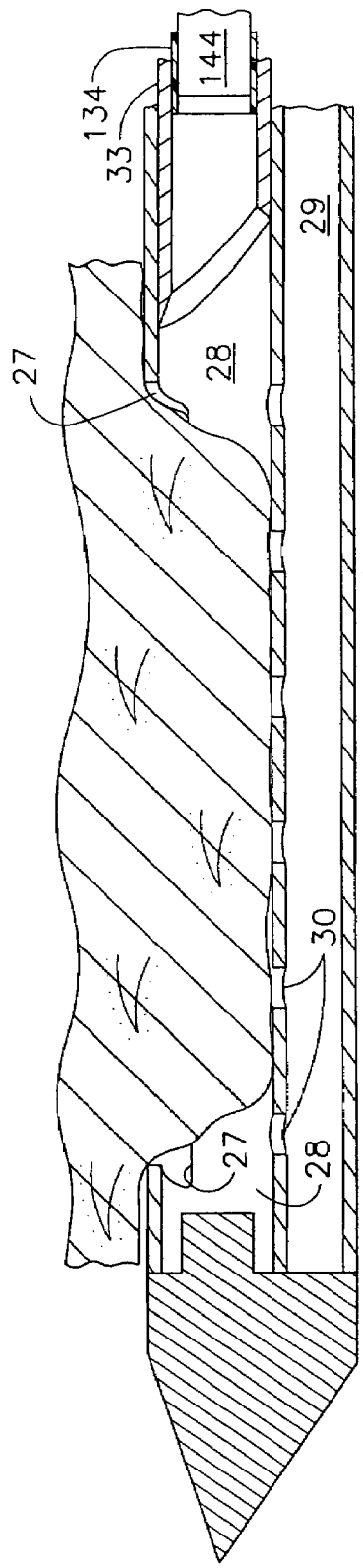
FIG. 21 presents a side longitudinal cross-sectional view of the probe as shown in FIG. 20, and after tissue has moved into the receiving aperture.
Figure 22:
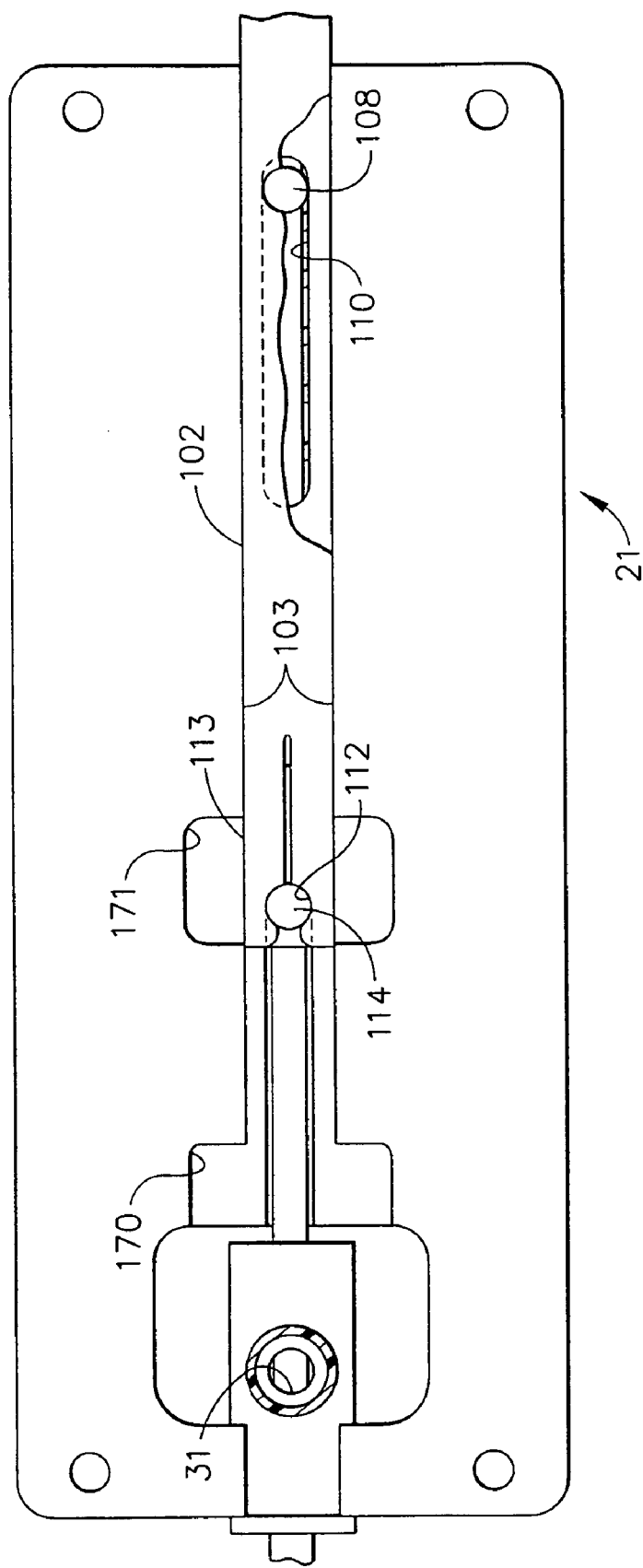
FIG. 22 presents a top sectional view of the body portion of the device as shown in FIG. 20.

FIGS. 20-22 depict the exemplary version of the device after the user has caused actuator 96 to be retracted rearwardly, after tissue has been drawn into the receiving aperture 27 of probe 24, and just before firing of the cutter 33 as will be described below. In order to move the device to this position, the user may pull or otherwise effect movement of actuator 96 in a rearward direction relative to body 21. As noted above, retraction member 102 and plunger 66 are integrally affixed to actuator 96, and so rearward movement of actuator 96 relative to body 21 effects corresponding rearward movement of retraction member 102 and plunger 66. Rearward movement of retraction member 102 effects reward movement of cutter 33 within probe 24, via engagement and pulling of nock 119 on firing pin 114. As firing pin 114 is pulled in a rearward direction, spring collar 116 with which it is integral is also pulled in a rearward direction, thereby pulling cutter 33 in a rearward direction to open receiving aperture 27, and compressing firing spring 118. The corresponding rearward movement of plunger 66 creates vacuum within syringe body 64, which is communicated through syringe nozzle 76, through vacuum tube 70, into vacuum source port 31 of probe 24, through vacuum lumen 29, through vacuum ports 30, and into cutter lumen 28, thereby drawing tissue into receiving aperture 27 as depicted in FIG. 21.

Figure 25:
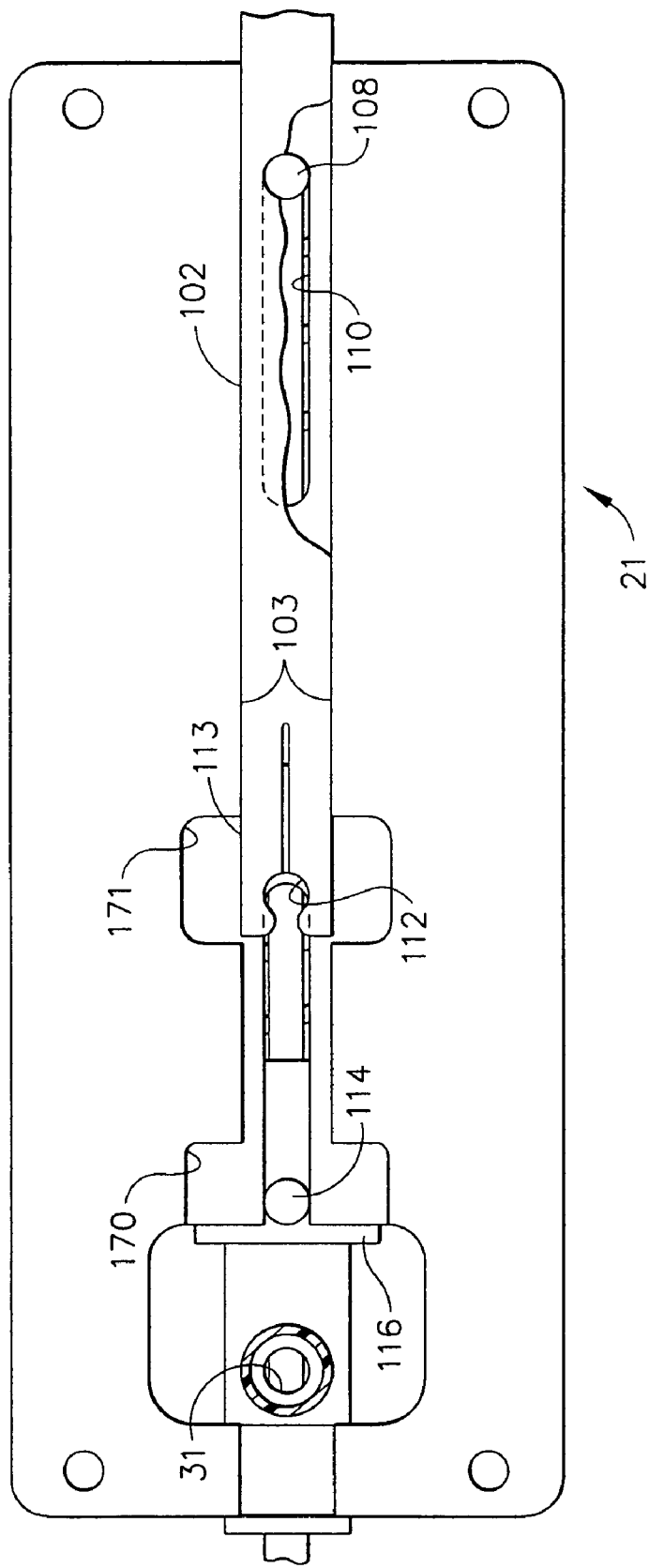
FIG. 25 presents a top sectional view of the body portion of the device as shown in FIG. 23.

FIGS. 23-25 depict the exemplary version of the device after release of the firing pin 114 and firing of the cutter 33 to sever and capture tissue within the probe 24. To effect release of firing pin 114 to release and fire cutter 33, the user may further pull or otherwise effect further rearward movement of actuator 96 relative to body 21, to move retraction member 102 the additional distance from the position shown in FIG. 22 to the position shown in FIG. 25. This moves flexible extensions 113 forming nock 119 past the distal edges of disengagement cavity 171, thereby allowing flexible extensions 113 to flex outwardly laterally to open nock 112 and release firing pin 114 under urging of firing spring 118 acting on spring collar 116. Urging of firing spring 118 moves cutter 33 and cutting tip 35 thereof forward past receiving aperture 27, effectively severing tissue drawn therethrough, and capturing the severed tissue within tissue lumen 34 of cutter 33 as depicted in FIG. 24. Rearward motion of retraction member 102 (and correspondingly, rearward motion of actuator 96) is limited to a rearwardmost extent by interaction of limiting pin 108 with track 110.

From a comparison of FIGS. 17-19, 20-22, and 23-25, it will be appreciated that the exemplary version of the device depicted provides for coordinated rearward movement of cutter 33 to a position ready for a cutting stroke, opening of receiving aperture 27 of probe 24, development of vacuum to draw tissues into receiving aperture 27, and compressing of firing spring 118, all effected by rearward movement of actuator 96. The last incremental rearward movement of actuator 96 effects release of firing pin 114 as nock 112 of retraction member 102 moves into disengagement cavity 171, and the resulting firing of cutter 33 in a forward direction under urging of firing spring 118 acting against spring collar 116. At the same time, plunger 66 of syringe 62 continues to be pulled rearwardly toward its rearwardmost position in order to maintain vacuum within the system during the cutting stroke. Thus, it will be appreciated that a single, effectively rapid, continuous rearward movement of actuator 96 effected by the user can effect the coordinated opening of receiving aperture 27, drawing of tissue into probe 24 by vacuum, and the severing of the tissue drawn therein, by cutter 33, in a short period of time before the vacuum within the device can substantially dissipate as the result of system leaks and/or drawing of body fluids into the probe 24 so as to allow the tissue to recede back out of the probe before it can be severed.

FIGS. 26-27 depict the exemplary version of the device as the collection tube 134 is being advanced forwardly to capture and collect a severed tissue sample. The user may advance collection tube knob 136 forward relative to body 21, thereby advancing collection tube 134 forward within cutter 33 so that it captures the severed tissue sample therewithin, as shown in progress in FIG. 27. As collection tube 134 is advanced, the severed tissue sample enters the distal end thereof, and either the severed tissue or a small quantity of air and/or fluid trapped between the proximal portion of the severed tissue and the distal end of ejector rod 144 will contact and urge ejector rod 144 rearwardly relative to collection tube 134 to make room for the tissue sample within the collection tube 134. After the tissue sample is captured within collection tube 134, the user may release collection tube knob 136, and under urging of return spring 138, collection tube knob 136 and correspondingly, collection tube 134 holding the severed tissue, will return to a predetermined position, with the distal end of collection tube 134 proximal to receiving aperture 27. Following that, the user may, by effecting movement of actuator 96 forward with respect to body 21, reset the device to the position shown in FIGS. 17-19 in preparation for drawing in and severing another tissue sample by repeating the steps described above. Alternatively, the user may entirely withdraw collection tube 134 from the device by pulling knob 136 rearwardly, and eject severed tissue sample (s) contained therein by advancing ejector rod 144 forwardly within collection tube 134, pushing the sample(s) out the distal end of collection tube 134. It will be appreciated that, following the severing of one or more tissue samples but prior to withdrawal of collection tube 134 and ejection of the samples, ejector rod 144 will move rearwardly relative to collection tube 134 as each sample moves into the distal end of collection tube 134, and the position of ejector rod 144 and/or ejector rod knob 146 with respect to collection tube knob 136 can thereby serve as an indicator of the amount of severed tissue and/or number of tissue samples contained within collection tube 134. Accordingly, ejector rod 144 may be marked with one or more visible indicators (not shown) to more effectively provide this information to the user.

Figure 28:
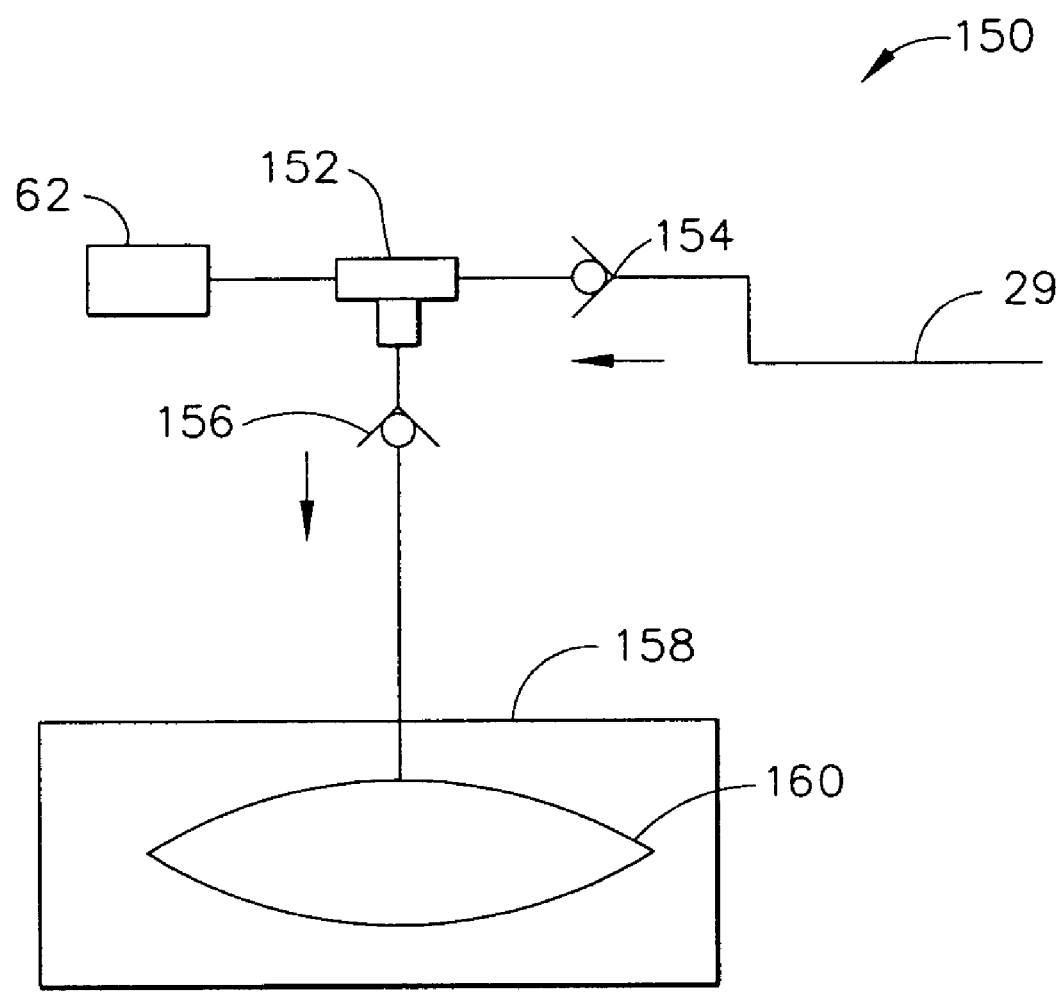
FIG. 28 is a schematic diagram of a version of a fluid management system that may be used with a device such as the device shown in FIG. 1.

In the exemplary version of the device 20 shown, the vacuum within the device created by the rearward movement of plunger 66 within syringe 62 can possibly cause air or other fluids to be drawn into the device via system leaks, or by drawing body fluids into receiving aperture 27 in addition to tissue, and such fluids can enter the vacuum system via vacuum apertures 30 and vacuum lumen 29 (see FIG. 4). In this event, it may be desirable to have a mechanism for venting, draining or expelling such fluids from the system (but not into the patient) in preparation for taking a successive tissue sample with the device in place. FIG. 28 schematically depicts one version of a system that can serve such a function. The exemplary fluid management system 150 includes a three-way junction 152 in the line of fluid communication between syringe 62 and vacuum lumen 29 of probe 24. One leg of three-way junction 152 may be vented to or placed in fluid communication by suitable tubing or other conduit mechanism with a receptacle 158 suitably configured to receive fluids vented, drained or expelled from the device. If a closed system is desired, fluids may be vented or expelled into an expandable bladder 160 via sealed connections, for purposes of, among others, avoiding an undesirable or counterproductive creation of back pressure within the receptacle 158. A first one-way check valve 154 lies in line between vacuum lumen 29 and three-way junction 152, such that it permits fluid flow away from but not toward vacuum lumen 29. A second one-way check valve 156 lies in line between receptacle 158 and three-way junction 152, such that it permits fluid flow away from but not toward three-way junction 152. From FIG. 28, it will be appreciated that this arrangement will allow fluid flow from vacuum lumen 29 of probe 24 and toward and possibly into syringe 62, but not vice versa, and this arrangement will allow fluid flow from syringe 62 and toward and into receptacle 158, but not vice versa. Thus, when syringe 62 creates a vacuum, it will draw fluid from the probe 24, but not from the receptacle 158, because such flow is prevented by second one-way check valve 156. If unwanted fluid is present in the system following a tissue severing stroke of the device, it may be expelled in part or in entirety by forward movement of plunger 66 within syringe 62, which will force fluid toward receptacle 158, but not toward vacuum lumen 29, because such flow is prevented by first one-way check valve 154. One-way valves 154, 156 and three-way junction 152 may be arranged and positioned within, on or about the device with suitable fluid conduit or passage structures such that a minimum quantity of unwanted fluid may remain in the system following expulsion by, for example, distal movement of plunger 66 in syringe 62.

It will be appreciated that the illustrated version of the fluid management system 150 is disclosed by way of example only and is not limiting. Further versions of the fluid management system 150 may include, for example, an exit tube coupled with one leg of junction 152 for the removal of fluid, which may, but need not necessarily, vent or drain into a receptacle. Receptacle 158 may, for example, comprise a vessel or container of any description, or an expandable bladder such as a balloon that simply expands as fluid is driven thereinto. Expandable bladder 160 may be, for example, any suitable bag, balloon, pouch, or flexible container.

Referring to the vacuum assembly 60 in the exemplary version depicted, it will be appreciated that any suitable mechanism that creates a vacuum, such as a syringe 62, other aspirator, or outboard vacuum source, may be used to supply vacuum to draw tissues into the probe 24 in accordance with versions described herein. It will be appreciated that various configurations, orientations and locations of the vacuum assembly 60 may be provided in accordance with the versions described herein. It will be apparent that the vacuum supplied by movement of an actuating member of an aspirator such as plunger 66, that draws tissue into receiving aperture 27 in the exemplary versions depicted, is supplied during or after opening of the receiving aperture 27 and before or during a cutting stroke. It will be appreciated that such vacuum may be supplied effectively while a receiving aperture is open, and effectively prior to and during at least a portion of the time a cutting edge moves across such receiving aperture in a cutting stroke, so as to provide that tissue is drawn into and present within a probe so that it can be severed in a cutting stroke. It will be understood, however, that simultaneous movement of a cutter and a plunger prior to a cutting stroke may be desirable in some circumstances for purposes of configuration of the driving mechanism(s) or other structures, but is not necessarily required to effect the proper timing of creation of vacuum within the probe. Accordingly, the respective motions of a plunger or other aspirator actuating member and a cutter may be decoupled and effected by separate mechanisms to provide for the creation of vacuum that is suitably timed with respect to a cutting stroke to ensure that tissue is drawn into a probe and situated in a position in which it can be effectively severed and removed by an associated device.

The exemplary version described and depicted herein involves a trip mechanism (the interacting combination of nock 112 on retraction member 102, and disengagement cavity 171 in retraction track 103) for alternately restraining, and then releasing, a member upon which a spring exerts force, to effect driving of components such as cutter 33. It will be appreciated that if springs or other devices having therein stored potential energy are used to supply motive forces, suitable trip mechanisms to alternately restrain and then release such devices may take a variety of suitable forms in addition to the example described and depicted herein.

Referring to the exemplary cutter driver mechanism 100, it will be appreciated that any suitable cutter driving mechanism, such as a rotational or non-rotational driving mechanism, may be used in accordance with versions described herein. In the exemplary components and versions described herein, the driving force to effect forward motion of the cutter 33 is supplied by a compressed spring, firing spring 118. However, it will be appreciated that such driving force can be supplied by any other suitable driving mechanism, such as but not limited to other types of springs in compression, tension, flexion or torsion, by other longitudinally motive devices such as gas or fluid cylinders or levers and/or gear-driven devices operably configured to store and release potential energy to supply longitudinal motive forces, or alternatively, to supply longitudinal motive forces by converting and/or transferring forces developed or supplied through other mechanisms. For example, suitable longitudinal forces might by supplied by hand-operated or motor-driven lever and/or gear mechanisms, used in conjunction with one or more spring devices, or not. A component such as actuator 96 or other component to transfer force and movement to charge a cutter driving mechanism may be manually actuated by a user or may, for example, be automated and/or part of an automatic system.

Referring to the collection assembly 130, it will be appreciated that any suitable tissue collection mechanism may be used in accordance with versions herein where, for example, the tissue samples may be removed immediately, or retained within an onboard receptacle other than a collection tube.

Having shown and described various versions and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings.

We claim:

1. A device for severing and removing internal tissues, comprising:
   a body comprising an actuation member;
   a vacuum assembly held by said body, wherein said vacuum assembly comprises a plunger affixed to said actuation member, wherein said plunger is operably configured to move integrally with said actuation member, wherein a vacuum is created by moving said actuation member and said plunger proximally;
   a hollow probe affixed to said body, said probe having a receiving aperture thereon, and a free distal end having thereon a sharp tip configured to pierce and penetrate tissue, wherein said probe further comprises a manifold providing a vacuum port connected in a substantially fluid-tight manner to said vacuum assembly via a vacuum tube;
   a cutter within said probe, having thereon a cutting edge having a concave grind, said cutting edge being proximate to said receiving aperture and said cutter being longitudinally movable within said probe such that said cutting edge may move past said receiving aperture, wherein the cutter has a spring collar integrally secured to the cutter, wherein the spring collar is configured to translate integrally with the cutter, wherein the cutter is engaged with the actuation member such that the cutter is configured to move integrally with the actuation member; and a firing spring substantially coaxial with said cutter, wherein a first end of the firing spring is engaged with the spring collar, wherein a second end of the firing spring is engaged with the body, wherein said firing spring is resiliently biased longitudinally to urge said cutter distally;

wherein proximal movement of said actuation member simultaneously moves the plunger proximally to create a vacuum, translates the cutter proximally, and compresses said firing spring longitudinally between the spring collar and the body, against the resilient distal bias of the firing spring;

wherein during a cutting stroke said cutting edge substantially translates past said receiving aperture and said cutter does not substantially rotate within said probe.

2. The device of claim 1, wherein said cutting edge is formed by a rotating grinder including a grinding surface having a convex shape.

3. The device of claim 1 wherein said cutter is formed from a tube.

4. The device of claim 3, wherein said cutter has a distal tip having a most distal extent and a most proximal extent, and said cutting edge is formed on said most distal extent.

5. The device of claim 4, wherein said cutting edge is formed by rotating grinder including a grinding surface having a convex shape.

6. The device of claim 5, wherein an angle formed by a line connecting said most distal extent and said most proximal extent, and a line perpendicular to the longitudinal axis of said tube, is from about 45 degrees to about 60 degrees.

7. The device of claim 1, wherein said cutter has a semi-circular transverse cross section.

8. The device of claim 1, wherein said probe defines a longitudinal axis, wherein said receiving aperture comprises a sharpened distal edge, wherein said sharpened distal edge is transverse to the longitudinal axis of said probe, wherein said sharpened distal edge cooperates with said cutting edge of said cutter in severing tissue during said cutting stroke.

9. The device of claim 1, wherein said cutting edge defines a sharpening angle, wherein said sharpening angle comprises an angle between said longitudinal axis and a line extending from said cutting edge along said concave grind, wherein said sharpening angle is from about 10 degrees to about 15 degrees.

10. The device of claim 1, wherein said cutting edge defines a sharpening angle, wherein said sharpening angle comprises an angle between said longitudinal axis and a line extending from said cutting edge along said concave grind, wherein said sharpening angle is from about 10 degrees to about 25 degrees.

11. The device of claim 1, wherein said cutting edge defines a sharpening angle, wherein said sharpening angle comprises an angle between said longitudinal axis and a line extending from said cutting edge along said concave grind, wherein said sharpening angle is about 14 degrees.

12. The device of claim 1, wherein said cutter has a substantially uniform cross section along its entire length.

13. The device of claim 1, wherein said hollow probe comprises a circular transverse cross-section and an inner wall, wherein said inner wall is configured to divide said hollow probe into a cutter lumen and a vacuum lumen.

14. The device of claim 13, wherein said inner wall comprises vacuum ports, wherein said vacuum ports are configured to allow fluid communication between said cutter lumen and said vacuum lumen.

15. The device of claim 1, wherein said hollow probe comprises a semi-circular transverse cross-section.

* * * * *